(12) United States Patent
Peyrard

(10) Patent No.: US 11,222,519 B2
(45) Date of Patent: Jan. 11, 2022

(54) PERSONAL SYSTEM FOR THE DETECTION OF A RISKY SITUATION, MORE PARTICULARLY OF A FALL PRONE SITUATION

(71) Applicant: ELLCIE-HEALTHY, Villeneuve Loubet (FR)

(72) Inventor: Philippe Peyrard, Villeneuve Loubet (FR)

(73) Assignee: ELLCIE-HEALTHY, Villeneuve Loubet (FR)

( * ) Notice: Subject to any disclaimer, the term of this patent is extended or adjusted under 35 U.S.C. 154(b) by 0 days.

(21) Appl. No.: 17/218,134

(22) Filed: Mar. 30, 2021

(65) Prior Publication Data

US 2021/0217286 A1     Jul. 15, 2021

Related U.S. Application Data

(63) Continuation-in-part of application No. 16/178,365, filed on Nov. 1, 2018, now Pat. No. 10,964,190, (Continued)

(30) Foreign Application Priority Data

May 31, 2016  (FR) ...................... 16 54922

(51) Int. Cl.
*G08B 21/04* (2006.01)
*A61B 5/00* (2006.01)
(Continued)

(52) U.S. Cl.
CPC .......... *G08B 21/043* (2013.01); *A61B 5/6803* (2013.01); *G06F 3/013* (2013.01);
(Continued)

(58) Field of Classification Search
CPC .............. G08B 21/043; G08B 21/0466; G08B 21/0453; G08B 21/0476; G08B 21/0492;
(Continued)

(56) References Cited

U.S. PATENT DOCUMENTS 5,689,241 A    11/1997  Clarke, Sr. et al.
5,745,038 A *   4/1998  Vance .................... G08B 21/06
                                                   340/575
(Continued)

FOREIGN PATENT DOCUMENTS

EP        2 061 026 A1    5/2009

*Primary Examiner* — Amine Benlagsir
(74) *Attorney, Agent, or Firm* — Im IP Law; Chai Im; C. Andrew Im

(57) ABSTRACT

A method for preventing and detecting a fall of a user and implementing a system including sensors and alarm, a pair of eyeglasses with hinged stems including rims for supporting glasses, worn by the user. The sensors are set in the hinged stems and the rims of the eyeglasses. The sensors include a triaxial accelerometer, an IR transmitter and an IR receiver of infra-red light both directed to the cornea of the user, and a barometric sensor. The triaxial accelerometer signal is acquired and processed to derive a walking pace parameter, a sit to stand parameter, a head posture parameter and an acceleration magnitude over the three axes. A composite index is computed based on the walking pace, the sit to stand and the head posture parameters. The alarm is generated if the first composite index exceeds a threshold.

6 Claims, 9 Drawing Sheets

Related U.S. Application Data which is a continuation of application No. 15/852,554, filed on Dec. 22, 2017, now Pat. No. 10,152,869, which is a continuation-in-part of application No. PCT/FR2017/051362, filed on May 31, 2017.

(60) Provisional application No. 62/667,515, filed on May 5, 2018.

(51) Int. Cl.
| | | |
|---|---|---|
| *G06F 3/01* | (2006.01) | |
| *A61B 3/00* | (2006.01) | |
| *A61B 8/00* | (2006.01) | |
| *A61B 5/0205* | (2006.01) | |
| *A61B 5/11* | (2006.01) | |
| *A61B 5/145* | (2006.01) | |
| *A61B 5/18* | (2006.01) | |

(52) U.S. Cl.
CPC ..... *G08B 21/0446* (2013.01); *G08B 21/0453* (2013.01); *G08B 21/0476* (2013.01); *G08B 21/0492* (2013.01); *A61B 3/00* (2013.01); *A61B 5/02055* (2013.01); *A61B 5/1103* (2013.01); *A61B 5/1114* (2013.01); *A61B 5/14532* (2013.01); *A61B 5/18* (2013.01); *A61B 5/7445* (2013.01); *A61B 5/7455* (2013.01); *A61B 8/00* (2013.01); *A61B 2503/22* (2013.01); *A61B 2560/0242* (2013.01); *A61B 2562/0219* (2013.01)

(58) Field of Classification Search
CPC . A61B 5/6803; A61B 5/02055; A61B 5/1103; A61B 5/1114; A61B 5/14532; A61B 5/18; A61B 5/7445; A61B 5/7455; A61B 2503/22; A61B 2560/0242; A61B 2562/0219; A61B 8/00; A61B 3/00; G06F 3/013
See application file for complete search history.

(56) References Cited

U.S. PATENT DOCUMENTS

| | | | |
|---|---|---|---|
| 6,147,612 A * | 11/2000 | Ruan | G08B 21/06 340/573.1 |
| 2001/0005230 A1 | 6/2001 | Ishikawa | |
| 2001/0028309 A1 | 10/2001 | Torch | |
| 2004/0000733 A1* | 1/2004 | Swab | G02C 5/146 264/1.7 |
| 2005/0251055 A1 | 11/2005 | Zhirnov et al. | |
| 2009/0105605 A1* | 4/2009 | Abreu | A61B 5/0046 600/549 |
| 2010/0134761 A1* | 6/2010 | Johns | A61B 5/163 351/209 |
| 2011/0221656 A1* | 9/2011 | Haddick | G06Q 30/02 345/8 |
| 2013/0010256 A1* | 1/2013 | Haddock | G02C 11/10 351/159.31 |
| 2013/0125406 A1 | 5/2013 | Delort | |
| 2013/0197856 A1 | 8/2013 | Barfield et al. | |
| 2013/0318776 A1* | 12/2013 | Jacobs | G06F 3/013 29/592.1 |
| 2015/0077697 A1 | 3/2015 | Gottardi et al. | |
| 2015/0354941 A1* | 12/2015 | Heaton | A61N 1/0452 607/48 |
| 2016/0165151 A1* | 6/2016 | Corlett | G06T 1/20 348/164 |
| 2016/0178904 A1* | 6/2016 | Deleeuw | G06F 3/011 345/8 |
| 2016/0262608 A1* | 9/2016 | Krueger | G06T 19/006 |
| 2017/0032646 A1* | 2/2017 | Alameh | G08B 21/0219 |
| 2017/0061758 A1 | 3/2017 | Sudo et al. | |

* cited by examiner

PERSONAL SYSTEM FOR THE DETECTION OF A RISKY SITUATION, MORE PARTICULARLY OF A FALL PRONE SITUATION

RELATED APPLICATIONS

This application is a continuation-in-part of U.S. application Ser. No. 16/178,365 filed Nov. 1, 2018, which claims benefit of U.S. Provisional Application 62/667,515 filed May 5, 2018 and which is a continuation-in-part of U.S. application Ser. No. 15/852,554 filed Dec. 22, 2017, which is a continuation-in-part of PCT/FR2017/051362 filed May 31, 2017, which claims priority from French Application 16 54922 filed May 31, 2016, each of which are incorporated herein by reference in its entirety.

FIELD OF THE INVENTION

The invention is about a personal system for the detection of a risky situation and alert. The invention belongs to the field of connected wearable devices capable of measuring physiological data of an individual.

As nonlimiting examples, such a risky situation involves cases of potential reduced alertness, following or preceding drowsiness, dehydration, loss of consciousness, or a fall.

More particularly the invention relates to connected eyeglasses featuring sensors for assessing the physiological state of an individual, with regard to specific risky situations, before said individual may feel any alerting symptom.

BACKGROUND OF THE INVENTION

Even a light fall, may potentially be a vital hazard when it affects an elderly or a disabled person.

Yet, the harmful consequences of a fall, even heavy, are mitigated if assistance is provided to the person in a short period of time. Other comparable cases concern, for example, seizures.

Falls are the leading cause of death in people over 65. Every second of every day in the United States an elderly falls, making falls the number one cause of injuries and deaths from injury among older Americans. In 2014 alone, older Americans experienced 29 million falls causing seven million injuries and costing an estimated $31 billion in annual Medicare costs.

Besides death cases, people who are victims of a fall usually experience a loss of autonomy and a loss of self-confidence that also have important consequences. Studies show that, in the case of an elderly person, the longer the time spent on the ground after a fall, the more serious the consequences.

OBJECT AND SUMMARY OF THE INVENTION

It is therefore an objective of the invention to be able to detect the fall of a individual, more particularly for older adults, especially during time when there is no one around to help, in order to call for rescue as quick as possible when potentially required.

It is also an objective of the invention to provide means for detecting a fall prone situation, that is detecting the physiological state of an individual that may lead to a fall, before the fall actually takes place.

Alertness disorder is an example of a situation that may lead to a fall, it may be the result of, e.g., an extreme fatigue, or more commonly, for elderly, the result of dehydration, drugs or alcohol consumption. Thus, in some instances, the detection of a loss of alertness and the warning of the person experiencing it, or of one of his relatives, may prevent a fall or mitigate its aftermath.

Dehydration, drowsiness and fall are connected together in many instances. Dehydration may cause dizziness and a loss or alertness, even a loss of consciousness leading ultimately to a fall. Dehydration is influenced by alcohol and drugs consumption, therefore an early detection of dehydration may in some instances prevent a further risk of loss of alertness. An early detection of a drop of alertness may prevent a fall. The severity of a fall, and the capability of the victim to recover herself from the fall may be assessed by measuring the alertness of the person after the fall.

Up to 30% of seniors aged 65 and above, who are admitted to the hospital are dehydrated, in 1.5% of the cases, dehydration is the primary cause for hospital admission.

Physiological measurements performed on groups of individuals in laboratory conditions can statistically detect signs of reduced alertness, sleep, fall, loss of consciousness or dehydration. These tests use multiple sensors that can be worn by an individual only in laboratory conditions. When the results of these experiments are used with the aim of developing a personal detection device, the detection quality usually drops, for various reasons, including:
- it is difficult to integrate suitable sensory, in terms of the number of sensors and their reliability of measurement, in a wearable device;
- the wearable device is unsightly, uncomfortable, too intrusive or too perceived by the individual and his relatives as a surveillance device, so that the individual does not wear it;
- the detection reliability is not satisfactory, because of the reduced number of sensors and, because it is based on statistical data not adapted to the individual itself and his way of life, leads to the generation of false alarms, so that, losing its confidence in the device, the user does not wear it anymore;
- the detection is too late, for instance, detecting an actual fall may be life-saving for the victim by alerting rescue on time but an earlier detection of a potential fall prone situation may help the person prevents the fall and its harmful effects by herself;
- the detection system usually uses cascading tests where the outcome of a first test determines the implementation of a second test, etc. when reliability is poor it only gets worse from one test to the other and generates positives false or negatives false; and
- the autonomy of the personal system is low because of the power consumption of the many components and of the required computing power.

While detecting a fall, a loss of alertness and a dehydration state may prevent many hazardous situations, there is a need for a broader fall prone situation detection that may or may not be combined with the risky situation detection as disclose in U.S. Pat. No. 10,964,190.

The invention pertains to a system based on an aesthetic sensor, autonomous and lightweight, specifically suited to its user.

The system and the method of the invention use a limited number of sensors, thus limiting the power consumption, but are capable of detecting a fall prone situation, an actual fall and an after-fall recovery.

Although the system is more particularly intended to the elderly, it is relevant to any individual, comprising healthy individuals.

To this end, the invention pertains to a method for preventing and detecting a fall of an individual and implementing a system comprising:

a pair of eyeglasses with hinged stems including rims for supporting glasses, worn by the individual and comprising a plurality of sensors and an alarm, the plurality of sensors being set in the hinged stems and the rims of the eyeglasses comprising:

a triaxial accelerometer;
an IR transmitter and an IR receiver of infra-red light both directed to the cornea of the user;
a barometric sensor;

wherein each sensor of the plurality of sensors is generating a signal, and is connected to a microprocessor configured to execute a computer program stored in a memory to collect and analyze data issued by the plurality of sensors, and to trigger alarms in response to an analysis of the data; and wherein the triaxial accelerometer signal is acquired and processed in order to derive form it a walking pace parameter, a sit to stand parameter, a head posture parameter and an acceleration magnitude over its three axes.

The method comprising the steps of:
computing a first composite index based on the walking pace, the sit to stand and the head posture parameters; and
generating a first type of alarm if the first composite exceeds a threshold. The sensors, thus arranged at the level of the head of the individual wearing the pair of eyeglasses allow not only to detect a fall but to detect a fall prone situation and to warn the individual or the caretakers when such a situation arises before the fall occurs.

By using at least two parameters for each kind of detection, each being derived from the detection of at least one pattern in the signal issued by at least one sensor, and combining them into a composite index, the robustness of the system is improved with regard to false alarms, either positive or negative, and can be tuned to be adapted to the individual wearing it.

The system may also comprise additional sensors according to specific embodiments. However, the use of a small number of sensors for the detection of a complex situation by a smart processing of the signal, allows a reduced power consumption and a broad operation autonomy, while maintaining a light weight for wearing comfort.

The installation of such sensors in a pair of classic eyeglasses, with foldable stems, enables the individual to wear the device in a discreet and aesthetic way. As compared to other personal systems of detection, such as wristbands or medallions, the installation of sensors in a pair of eyeglasses favors a nearly continuous wearing of said sensors by the user during its hours of activity, most of users being used to wear their eyeglasses as soon as they wake up.

The composite index may be computed from more than two parameters but uses at least two parameters derived from the signals issued by the sensors and collected by the processing and calculation unit.

Depending on of the risk to be detected and assessed, the two parameters are either derived from the signal issued by the same sensor or from the signals issued by two different sensors.

Advantageously, one of the two parameters is relevant in the context of references specific to the individual wearing the eyeglasses and the second parameter is relevant regardless of the individual.

Usually, but not necessarily, the first parameter is indicative of an early stage of the risk while the second parameter is indicative of a more advanced stage of risk. Therefore, the combination of both information in the composite index allows said composite index to be adapted to the individual, by a preliminary measurement and/or through a machine learning mechanism, while the taking into account of the second parameter provides a safety net in case of a hard issue.

Therefore, the accuracy and the reliability of the detection and of the trigger of a given alarm level are improved.

Throughout the text the term 'or' must be interpreted as inclusive (and/or).

The invention is advantageously implemented according to embodiments and variants exposed hereunder, which are to be considered individually or in any technically operative combination.

The method uses the same set of sensors to detect a fall, whether soft or hard, of the individual and to this end comprises the steps of:
acquiring a signal of the barometric sensor;
computing a second composite index based on:
an acceleration magnitude combined along three axes of the triaxial accelerometer;
a variance of the acceleration magnitude over a predetermined duration;
an acceleration component over an axis of the three axes of the triaxial accelerometer parallel to gravity;
the acceleration magnitude combined over the three axes of the triaxial accelerometer in a plane perpendicular to the gravity;
a variation of a barometric pressure between two moments; and
generating a second type of alarm corresponding to the detection of a fall if the second composite index exceeds a threshold.

Furthermore, once a fall is detected the method uses the same set of sensors to assess the recovery of the fallen individual, and to this end comprises the steps of:
controlling the IR transmitter, collecting and processing a signal from the IR receiver;
processing the signal of the IR receiver for detecting a closure and an opening of an eyelid of the individual;
computing an alertness composite index based on the opening and closure events of the eyelid;
when a second type of alarm is generated:
computing a third composite index based on:
a body posture parameter derived from the head posture parameter and the barometric sensor; and
the alertness composite index; and
generating a third type of alarm when the third composite index exceeds a threshold.

Advantageously, the method of the invention comprises a step of controlling that the eyeglasses are worn by the individual by performing a check out test that comprises the steps of activating the IR transmitter and analyzing the IR receiver signal in response.

According to a preferred embodiment, the computation of the walking pace parameter comprises:
projecting the signals issued by the triaxial accelerometer on an axis parallel to the gravity direction to obtain a pedometer signal;
obtaining a threshold value and detecting consecutive peaks in the pedometer signal exceeding the threshold, during a given assessment time;
measuring the time separating 2 consecutive peaks during the measuring time;
computing the variance of this time over the assessment time; and
using this parameter as part of the first composite index.

According to this embodiment, the method further comprises the steps of:
  assessing an angle of the head posture variation of the individual during the assessment time;
  obtaining a threshold angle and measuring the time the angle exceeds this threshold during the measuring time; and
  using this parameter as part of the first composite index.

Further parameters are computed based on the sit to stand movements of the individual.

According to an exemplary embodiment, the method of the invention further comprises the steps of:
  detecting a sit to stand event by a specific pattern in the signals issued by the sensor comprising an acceleration parallel to the gravity axis;
  measuring the duration of the sit to stand event;
  measuring the peak acceleration during the sit to stand event; and
  using these parameters as part of the first composite index.

Advantageously, the method further comprises:
  counting the number of sit to stand events per day; and
  using this parameter as part of the first composite index.

DESCRIPTION OF THE DRAWINGS

The invention is described hereunder according to its preferred embodiments, in no way limiting, and with reference to FIGS. 1 to 18, in which.

DETAILED DESCRIPTION OF THE EMBODIMENTS

Figure 1:
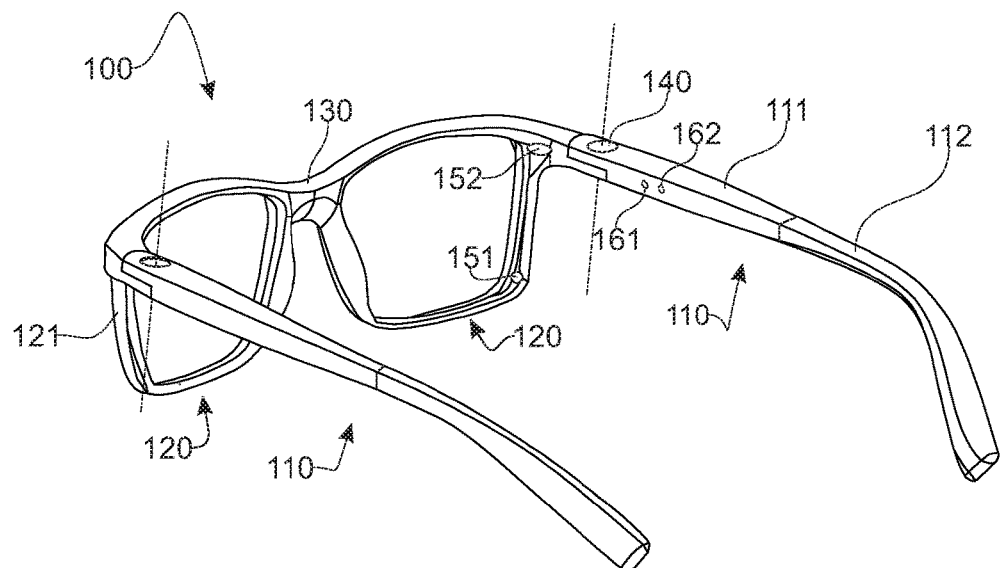
FIG. 1 is a perspective view of an exemplary embodiment of the eyeglasses of the system of the invention.

FIG. 1, according to an exemplary embodiment, sensors of the system of the invention are borne by a pair of spectacles (100), featuring two hinged stems (110), two rims (120) holding prescription or not lenses, said rims (120) being linked by a bridge (130) resting on the nose of the user when the spectacles are worn. According to this exemplary embodiment, the stems comprise two parts. A first part (111), so-called front part, extends from the stem hinge (140) along about half of the stem length. The second part (112) of the stem, so-called aft part, is connected to the first part (111) e.g., by clipping. This second part rests on the ear of the user, and include or not a curved temple tip, also called earpiece, pursuant to different styles of eyeglasses.

According to this exemplary embodiment, the front part of the stem bears electronic modules, while the second part (112), or aft part, does not include any electronics. Therefore, this second part is adapted to the morphology of a user like for any conventional eyeglasses, by using a shorter or a longer second part (112), or even by distorting it by heating. Similarly, the rims comprise two parts, the outer part (121) of the rims, extending substantially between the hinge and the basis of the rims, bears sensors, including an IR transmitter (151) and an IR receiver (152). The lower part and the inner part of the rims (120), up to the bridge (130), are free from any electronics and eases the mounting of any type of lens.

According to this exemplary embodiment, the rims are made of plastic and fully surround the lenses. As a for instance, the lenses are set up in the spectacles by heating the lower part of the rims and their connections to the bridge. However, the design of the spectacles of the system of the invention authorizes the use of other types of rims between the outer part (121) and the bridge (130), such as metallic rims or wire type rims. According to this exemplary embodiment the nose-pads are integrated to the rims and the bridge.

However, the design of the spectacles, in the same way that it allows the fitting of other types of rims, also allows the set-up of nose-pads hinged on pad arms, which then can be adjusted in the same way as for conventional eyeglasses. Therefore, the spectacles of the system of the invention are adaptable to the morphology of their user, like conventional eyeglasses, to achieve optimal wearing comfort and stability.

The eyeglasses are therefore suited to any type of lenses, prescription or not, simple, bifocals or progressive, or simply fashionable. They allow, in addition, different variations of style to match their aesthetic with the taste of the user. The mounting of the lenses as well as the mechanical adjustments of the eyeglasses of the system of the invention are preferentially performed by a professional, e.g., an optician, according to known techniques, similar to the techniques used for conventional eyeglasses.

Electronic modules are distributed between the front (111) parts of the left and the right stems and are connected by a flexible bus running through the upper parts of the rims and the bridge (130).

Figure 2:
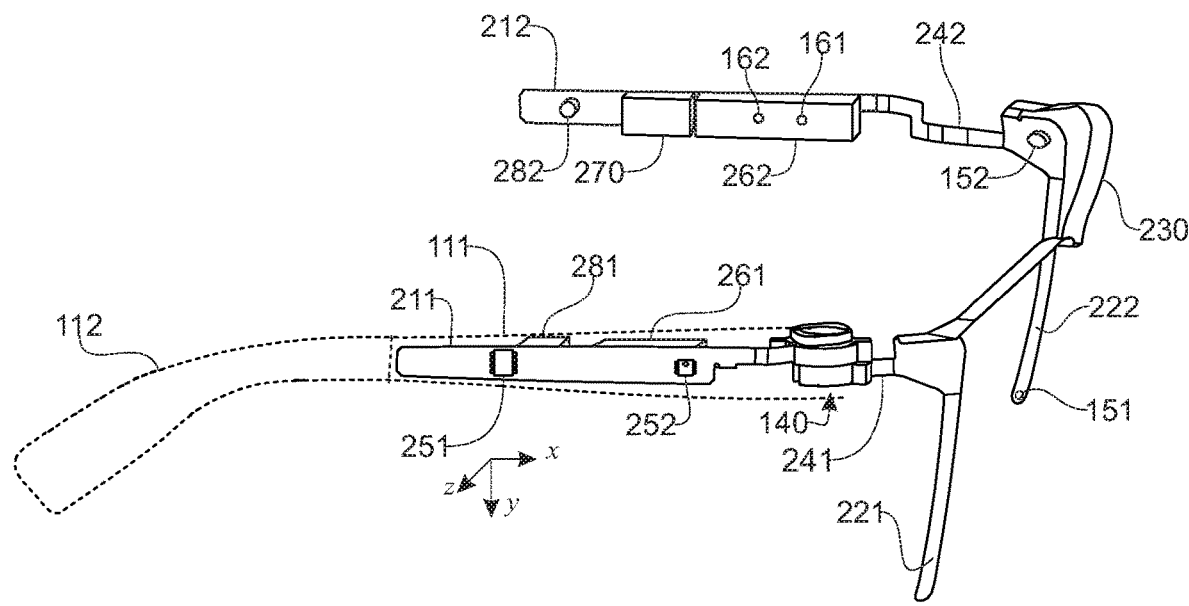
FIG. 2 shows in a perspective view, an exemplary embodiment of the arrangement of electronics within the frame of the eyeglasses of the system the invention.

FIG. 2, according to an exemplary embodiment, the eyeglasses of the system of the invention comprise several circuit boards (211, 212, 221, 222), on which the various sensors, acquisition and calculation means as well as data transmitting means, are welded or snapped.

According to this exemplary embodiment, the electronic boards are housed inside the front part of the stems and inside of the outer parts of the rims. As a for instance, those parts of the stems and rims are made of a plastic material such as a polyamide or acetate or of a composite material comprising a thermosetting or thermoplastic matrix reinforced by a fibrous charge of glass, of carbon or of natural fibers such as bamboo or linen, for more lightweight and strength.

These envelopes provide both mechanical shielding and weatherproof of the electronics, and are available in different colors, different surface textures and different shapes.

The electronic boards (211, 212, 221, 222) are connected to each other by flexible buses (241, 242, 230), comprising a central bus (230) extending between the right side and the left side of the spectacles and running through the inside of the upper parts of the rims and the bridge, and side buses (241, 242) connecting the boards (211, 212) located inside the front parts of the stems and the boards (221, 222) located inside the outer edges of the rims. The side buses (241, 242) are running through the hinges (140) of the stems, said hinges being specifically designed for this purpose.

Thus, the functions of measurement, signal processing, calculation, data transmission and power distribution are essentially distributed between the two stems, so as to balance the weight distribution between the two sides of the eyeglasses frame.

The sensors used are of the ultra-miniaturized type also known as "MEMS" or "NEMS".

According to one embodiment, the eyeglasses comprise an IR transmitter (151) and an IR receiver (152), set on an electronic board (222) within the outer edge of a rim. The transmitter and the receiver are oriented towards the eye of the user.

In another embodiment, the same layout is set in both the left rim and the right rim. Doubling of the device allows for measurements on each eye in order to assess the consistency of the obtained signals, and to only use the signals issued by one of the transmitter-receiver couple, in the case of malfunction of the other.

These sets of IR sensors (transmitter and receiver) are used to measure eye blink frequencies and eyes closure in order to assess the level of alertness of the person wearing the glasses.

They may also be used to measure the IR light absorption of the blood conveyed by the blood vessels in the eye, either under the sclera or in the eyelid. The pattern of absorption of IR light by the blood can be correlated to the hydration state of the person.

To this end, the emission power of the IR receiver is increased at regular time intervals, for instance, every 10 minutes, in order to measure the IR absorption pattern of the blood and assess the dehydration state of the person.

The reflectance of the eye is also a function of the hydration of the eye, which in turn is an indicator of the dehydration state of the person. This reflectance may also be measured by means of the IR transmitter and the IR receiver.

These parameters: IR absorption pattern of the blood and reflectance change from one person to another, therefore a calibration or an adaptation are required for deriving a parameter and a severity index based on these measurements.

Additionally, the dehydration state of the person may also be measured through the voltage response of the skin impedance circuit. This parameter is less sensitive to the individual as compared to the former ones.

To this end, the eyeglasses of the invention may comprise two electrodes made e.g., of copper that are here shown as circular electrodes, but can take any other suitable shape, such as strips.

A low voltage sine wave generator, as for instance producing a 3 volts sine wave at 50 kHz, is connected to one electrode (161) and the alternative current is transmitted to the other electrode (162) by the skin, thus allowing to measure the impedance of the skin by inserting a sensor in the circuit.

The electrodes are set on the front part of a stem in such a way that they contact the skin of the user wearing the eyeglasses.

The impedance variation of the skin at such a frequency results from resistance and capacitance variation with the hydration level. The impedance measurement is in the range of a few hundreds of ohms, e.g., 200 to 500 ohms.

The value corresponding to a well hydrated subject can be calibrated and stored in the memory means of the device.

In an alternative embodiment, impedance measurements may be performed at various frequencies of the supplied current alternative current. Capacitance variations are more sensitive in the lower frequency range, i.e., in the kHz range, while resistivity influences the results in the 10 kHz range.

A drop of about 10% from the nominal value of the impedance thus measured, indicates a dehydration state.

Such measurements may be performed on regular time intervals, e.g., every 30 minutes.

A triaxial accelerometer (251) is set on one of the electronic boards included in the stems, i.e., on the electronic board (211) located in the right stem according to the exemplary embodiment shown in FIG. 2. The accelerometer measures accelerations in three directions (x, y, z).

According to this nonlimiting example, said accelerometer is mounted so that the acceleration of gravity is oriented pursuant to the positive y axis when the eyeglasses are worn by the user, that is to say, substantially parallel to the direction of the gravity if the user is standing and looking straight in front.

According to another embodiment, the accelerometer sensor is included in a so-called inertial MEMS, comprising a triaxial accelerometer and a gyro sensor. According to yet another embodiment, the accelerometer is included in a MEMS, comprising a triaxial accelerometer, a gyro sensor and a magnetic compass.

Advantageously, the sensor comprising the accelerometer includes an integrated temperature probe, making it possible to correct the signal gain and linearity according to the sensor temperature.

As a nonlimiting example, the accelerometer has an amplitude of measurement of ±6 g (±58.86 ms$^{-2}$) on each axis.

According to a specific embodiment, a second triaxial accelerometer (not shown) is set on the electronic board (212) of the left stem of the eyeglasses. The combination of the two accelerometers signals allows to improve the accuracy of the measurement of rotational head movements and to better differentiate these movements from movements of the whole body of the user.

The second accelerometer is preferably set on the other stem in symmetry with the first one. Head movements, like flexion-extension (movement of the "yes" head sign), axial rotation (movement of the "no" head sign), or of side inclination, in the accelerations projecting in opposed signs on the axes of the two accelerometers.

Thus, for example, while referring to the (x, y, z) system of FIG. 2, a side inclination results in opposite projections of the acceleration on axes y and z of the two accelerometers.

An axial rotation of the head results in opposite projections of the acceleration according to axes x and z of the two accelerometers. The combination of this information with information from the gyro sensor and the magnetic compass, in an embodiment featuring these types of sensors, allows to detect complex posture changes of the user.

A barometric sensor (252) is set on an electronic board (211), according to this example on the electronic board located in the right stem, but alternatively on the electronic board (212) located in the left stem. Such a MEMS sensor can commonly detect a pressure variation of about 6 Pa, which corresponds to a variation of altitude of approximately 20 inches (50 cm). Processing the signal of such a barometric sensor, allows for example to detect a position change of the user, e.g., from a standing position to a sitting or lying position, and vice versa, when said user wears the eyeglasses of the system of the invention.

The risky situations whose detection may be performed; loss of alertness, dehydration, fall prone situation, fall, and fall recovery, are detected by combining information issued from the processed signals of:
  the IR receiver (152), excited by the IR transmitter (151);
  the triaxial accelerometer (251);
  the barometric sensor (252); and
  the skin impedance measurement through the electrodes (161, 162).

The detection reliability is improved by adding to these sensors:
  a second IR transmitter and receiver couple;
  a second triaxial accelerometer mounted symmetrically to the first on the other stem of the eyeglasses; and
  a second pair of electrodes either on the same stem but located in a different area, or on the other stem, the second pair of electrodes being of a different shape.

In this embodiment one pair of electrodes may be supplied by an alternative current in the 1 kHz-9 kHz range, while the other pair of electrodes is supplied by an alternative current in the 10 kHz-90 kHz range.

The detection reliability is further improved, as well as the capability of discriminating more finely some situations, by adding to the previous sensors:
  a gyro sensor; and
  a magnetic compass.

These lasts two sensors, are advantageously integrated, alone or in combination, in a MEMS also comprising a triaxial accelerometer.

More specifically a fall prone situation is detected by combining the information issued by the processed signals of:
  the triaxial accelerometer
  the barometric sensor A fall is detected by combining the information issued by the same sensors but with a different processing.

Therefore, these two sensors are the only one required, if the purpose of the eyeglasses is limited to fall prevention, which allow to make economic eyeglasses with a very low power consumption for such a specific application.

Adding the IR emitter and receiver allows to improve the relevance of the alarm generation by reducing negative and positive false, and also adds the capabilities of after fall recovery assessment and of alertness assessment.

Therefore, starting from the same base, the pair of eyeglasses may be customized for various applications, either by adding or by removing sensors or by uploading a specific software implementing a specific method and using part or all of the sensors and the information they issue. The processing and calculation unit is advantageously distributed between two modules (261, 262) set respectively on the electronic boards of the right stem and the left stem.

As a nonrestrictive example, the module (261) of the right stem comprises a microprocessor and memory means, including a program for acquiring the signals from the sensors, and for processing signals and calculating the relevant parameters, whereas the module (262) of the left stem, collects the signals of the sensors placed on this same stem and their transmission towards the module of the right stem, manages the power supply, including the current supply to the electrodes if implemented, the charge of the battery (270) and the communications, whether wired or wireless with other devices, in particular towards a smartphone, a computer, or a WiFi® gateway.

The eyeglasses finally comprise means of alarm distributed between the stems, for example a colored led (282) and a buzzer (281).

According to an embodiment a miniaturized connector (not represented), for example of the micro-USB type is integrated in one the stems and allows data exchange with other devices, via a wire connection, and the recharging of the battery (270).

In a specific embodiment the module (261) comprising the microprocessor also comprises a geolocation chip.

By using a limited number of sensors and highly integrated electronics, the weight of the eyeglasses is kept under 1.4 oz (40 grams) without the lenses, with an operating autonomy of at least 8 hours per battery charge.

Advantageously, the eyeglasses of the system comprise foldable stems, in order to be used, carried and tidy up like any conventional eyeglasses, more particularly to allow their tidy up in a case in order to protect the lenses when the user is not wearing said eyeglasses.

The distribution of the electronic modules between the right stem and the left stem, implies that a bus connects the electronic boards of the two stems and runs through the hinges of the stems. For this purpose, the eyeglasses of the system of the invention feature specific hinges guiding the bus during the folding and unfolding of the stems so that it follows a high enough radius of curvature avoiding any damage to said bus.

Figure 3:
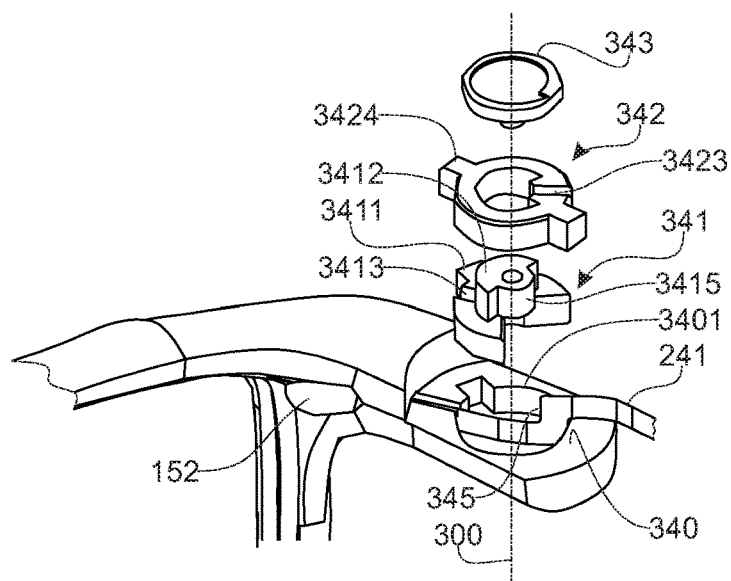
FIG. 3 shows, according to a partial exploded view in perspective, an exemplary embodiment of the hinge of the stems of the eyeglasses of the system according to the invention.

FIG. 3, an exemplary embodiment of the right stem hinge of the eyeglasses of the invention is shown in a position corresponding to the unfolded stem. The stem is supported by a shouldered bearing surface (340) at the end of the rim, making its precise vertical positioning according to the hinge rotation axis (300). The joint is performed between a hub (342) connected to the stem and an axle (341) housed in the fixed part of the frame forming the aforementioned bearing surface (340).

The axle (341) comprises two parts connected to each other, the first part (3411) is fitted in a bore (3401) of complementary shape, made in a fixed part of the frame, and the second part (3412), of smaller diameter, around which the hub (342) revolves. The first part of the axle is indexed in rotation in the bore, for example, by means of a tenon and mortise assembly and fixed, for example, by clipping or gluing.

The bus (241) is running in the stem and goes down in the bore (3401) receiving the axle (341) by a shoulder to reach the rim. For this purpose, the first part (3411) of the axle comprises a slit (3413) as a passageway for the bus (241). This first part (3411) of the axle extends on approximately ¾ of a circle the open part providing a clearance equal or slightly higher than 90° for the movement of bus (341) in the bore (3401) when folding and unfolding of the stems.

The hub (342) is set up in the stem, and also comprises a slit (3423), as a passageway of the bus part (241) located in the stem behind the shoulder (345), the aforementioned slit (3423) being appreciably diametrically opposed to the slit (3413) of the axle when the stem is unfolded.

The aforementioned hub is snapped in a bore of complementary shape, in the stem, indexed in rotation relative to said stem, for example by means of a tenon and mortise assembly, and fixed in said bore, for instance by clipping or gluing.

During the folding of the stem, the part of the bus (241) entering the slit (3413) of the axle does not move, only the part in the slit (3423) of the hub does, up to the bus shoulder (345). The second part (3412) of the axle comprises a portion (3415) of lower diameter than the diameter of the portion guiding the pivot join, the shoulder (345) of the bus glides on this portion of lower diameter during the pivoting of the stem. Thus, the radius of this lower diameter portion defines the radius of curvature imposed on the bus (241) when folding and unfolding the stems.

The whole assembly is held in position by a rivet (343).

Advantageously, an indexing mechanism is included in the tenon of the axle that stops the axle in rotation in the bore (3401). The hub comprises a tenon (3425) cooperating with this indexing mechanism to index the stem in the unfolded position and to avoid any damaging of the bus (241) by too important an aperture, because the location of the IR receiver (152) does not make it possible to limit this angular displacement by an abutment of the stem on the rim, as that is usually carried out for conventional spectacles.

According to an exemplary embodiment, the eyeglasses of the system of the invention operate in a completely autonomous way, by determining the parameters related to a given risky situation and by generating alarms towards its own means, from an analysis of these parameters performed by the microprogram stored in the processing and calculation unit.

Figure 4:
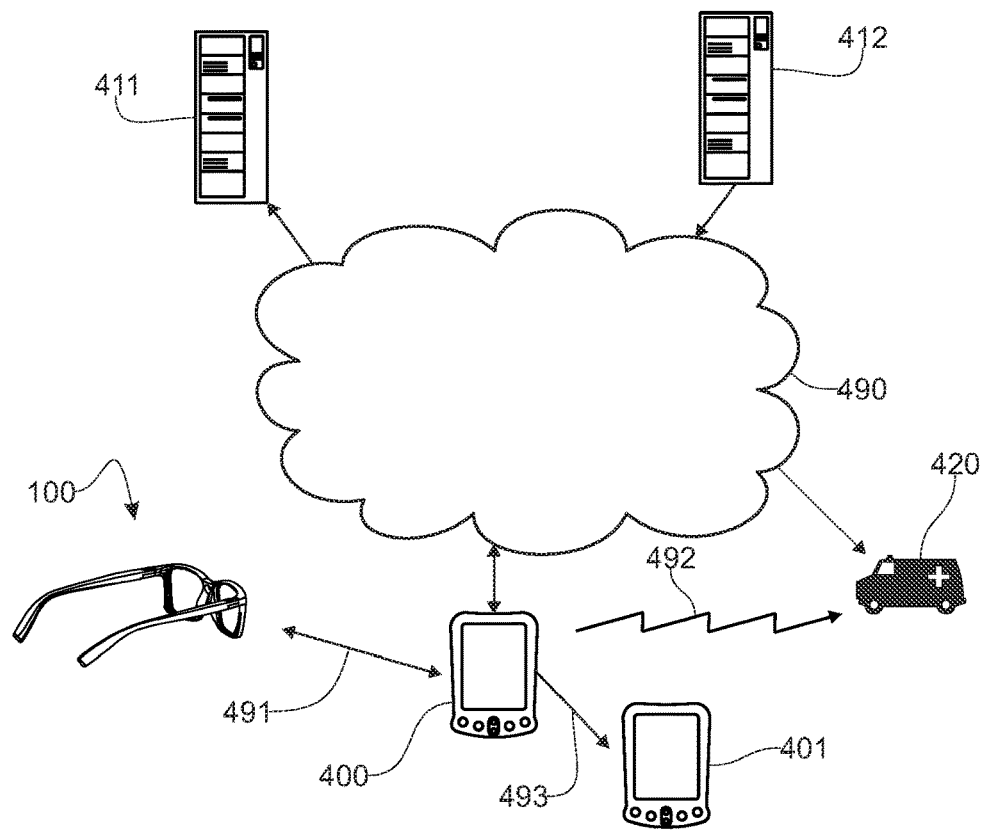
FIG. 4 is a scheme showing an exemplary embodiment of the system of the invention in its so-called connected version.

FIG. 4, according to another embodiment of the system of the invention, the eyeglasses (100) are said connected, and have the ability to communicate either permanently or periodically with another object (400) by a connection (491) either wireless, e.g., of the Bluetooth® low energy or Zigbee® types, or by wire.

As of some examples, the connected object (400) is a smartphone, a personal computer or a WiFi® gateway. This object (400) is in turn connected to one or more networks, and to other objects (401) or servers (411, 412), for example via internet (490), a cellular network (492) or a proximity wireless link (493) like a Bluetooth® link.

This embodiment makes it possible to increase the functionalities of the system. Thus, the connected object (400) is able to download an update of the microprogram from an update server (412) and to upload said update in the processing and calculation unit of the eyeglasses once paired with it.

The aforementioned connected object advantageously comprises its own means of calculation and a specific program allowing an analysis of the data collected from the memory means of the eyeglasses, then, by analyzing these data, adjusts the eyeglasses operation according to the user, in particular the thresholds of alarms triggering, or the calculation parameters of these thresholds.

The same program comprised in the connected object (400) is also able to conduct tests aiming at checking the correct operation of the connected glasses or detecting and fixing malfunctions.

For example, when the eyeglasses are comprising two couples of IR transmitter-receiver on each rim, if an abnormal or suspect operation of one of the couples is detected, the assessment of alertness is then based on the sole signals issued by the couple operating correctly. The same applies when the pair of eyeglasses comprise two or more sets of two electrodes.

According to a specific embodiment, the connected object (400) is also capable of transmitting alarms to third parties, through various connection routes, such as Internet, a proximity network or a cellular network.

As a for instance, in the case of a serious fall detection, it sends an alert to a rescue center (420), along with the geolocation of the person wearing the eyeglasses. According to another example of implementation, the connected object (400) sends an alert of reduced alertness of the wearer of the eyeglasses to the smartphones (401) of people in its vicinity. Therefore, the passengers of a vehicle driven by the user are warned about its condition and urge him to stop driving.

According to yet another example, the drop of alertness alarm is sent, for example, via a cell phone network or a DECT network, to the remote supervisor of an operator driving a machine or an industrial gear and wearing the eyeglasses.

In still another embodiment, the information of a detected event such as a drop of alertness or a fall, of substantial severity, is sent to an assistance center, via the internet or via a cell phone network, along with the geolocation of the device. This geolocation can either be retrieved directly from the eyeglasses if they are equipped with a geolocation chip, or from the connected object (400) such as a smartphone, paired with the eyeglasses.

Upon receipt of this information, the assistance center may enter in contact with the user, e.g., through the smartphone (400), either by a voice or a text communication in order to check out the condition of the user, or to help him staying alert for a limited duration, and guide him to the nearest place to stop and have a rest.

Accordingly, the eyeglasses (100) are associated with a single number of identification (UUID) and, through an application set up in the connected object, to information relating to the user, such as its age, its possible pathologies, or information derived from the data acquisition carried out by the eyeglasses, such as its average frequency of spontaneous eye blinking.

This information, combined with data from the measurements carried out by the eyeglasses, is transmitted periodically, for example once a day, and in an anonymous way to a server (411) collecting whole of these data.

Therefore, this server gradually builds a large database, on which statistical studies implementing artificial intelligence, commonly referred to as the "Big Data", are carried out and used to improve the system and to offer custom updates.

Accordingly, the system implements a machine learning process and adapts specifically to its user. This adaptation comprises two levels. A first level is achieved at the level of the device itself, i.e., the eyeglasses, by implementing its own means of calculation and allows to adapt the conditions of alarm to the own characteristics of the user without changing the processing algorithms. A second level is reached through population analysis and helps to refine the algorithms by detection category and phenotype. This second level is implemented in a remote server (411).

Figure 5:
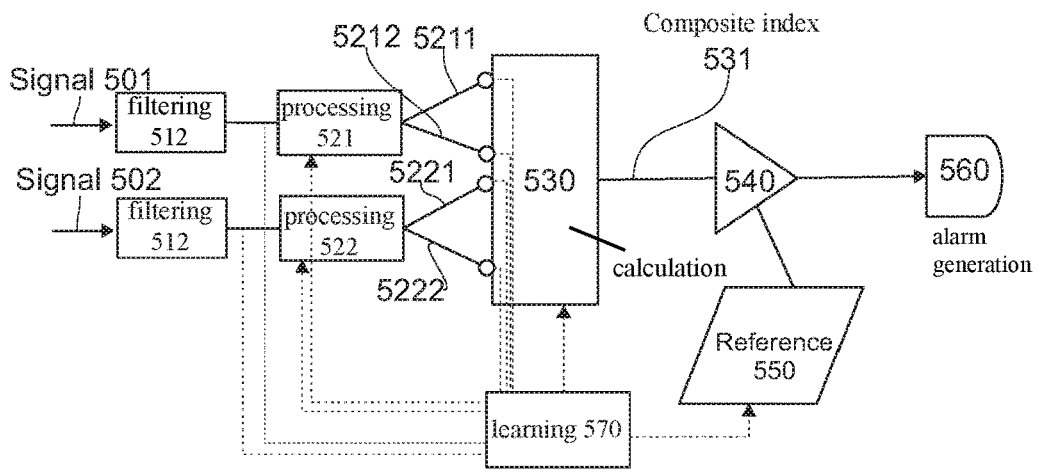
FIG. 5 is a flow chart of an example of signal processing leading to the generation of an alarm.

FIG. 5, according to an exemplary embodiment the generation of an alarm pertaining to a given risky situation, takes into account the signals (501, 502) issued from one or more sensors. The signal issued by each sensor undergoes a filtering step (511, 512) that is specific to each type of sensor in order eliminate the noise and irrelevant influences.

During a processing step (521, 522) a series of parameters (5211, 5212, 5221, 5222) is extracted from each signal. These parameters are combined during a calculation step (530) in order to define a composite index (531) relating to the kind of monitored situation.

This composite index (531) is then compared (540) with a reference (550) stored in memory, and if it differs from this reference by a significant level, an alarm is generated (560).

The steps of processing (521, 522), calculation (530) and comparison (540) implement constants that are stored in the memory means of the processing and calculation unit. Several of these constants are specific to the wearer of the eyeglasses. Therefore, in parallel to the processing of alarms, in the course of a learning step (570), signals and parameters calculated at the processing step (521, 522) are analyzed, and the constants used for processing, calculation and comparison may be changed by an authorized magnitude, in order to adapt to the individual wearing the eyeglasses, this method corresponding to the first level of machine learning and customization of the system.

Figure 6:
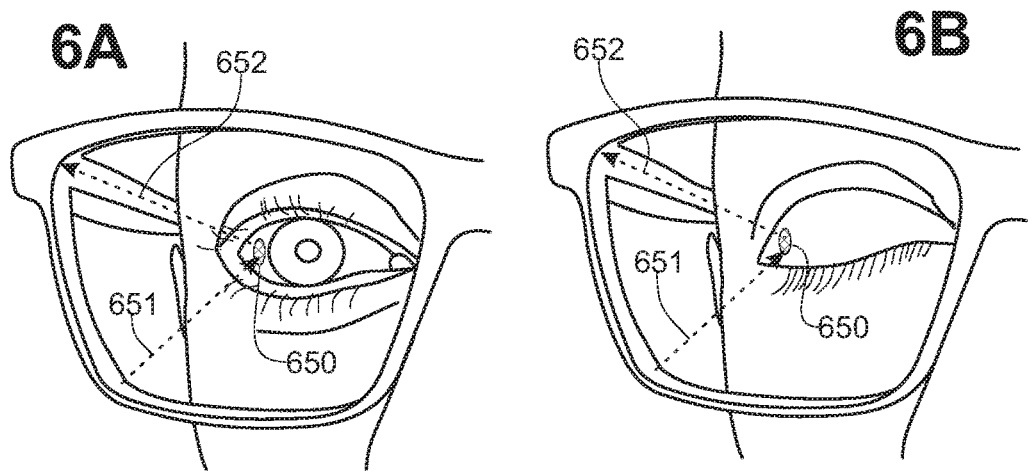
FIG. 6 shows, according to a perspective view, the operation of the transmitter and the receiver of the system of the invention, with the eye open in FIG. 6A and with a closed eye in FIG. 6B.

FIG. 6, the alertness measurement and the related generation of alarms is essentially based on the analysis of the spontaneous eye blinks supplemented by the detection of a head drop. The measurement of eyelid blinks is carried out from the signal issued by the IR receiver.

FIG. 6A, when the eye is open, the beam of incident light (651) generated by the IR transmitter is reflected in a light spot (650) on the cornea, the IR receiver measures the intensity of the reflected beam (652).

FIG. 6B, when the eye closes, the incident beam (651) is reflected on the eyelid. The reflectance of the eyelid being different from that of the cornea, the light intensity of the reflected beam (652) is different.

Thus, the intensity of the reflected signal (652) varies according to the eyelid surface lighted by the bright spot of the incident beam (651). The reflectance of the eyelid is higher than that of the cornea, so the more the eyelid closes the higher the intensity of the reflected signal (652) thus measured by the IR receiver.

Figure 7:
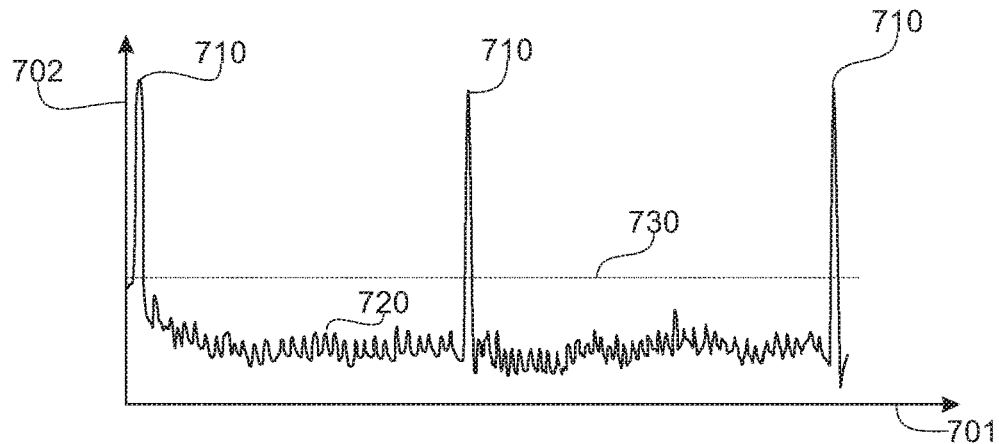
FIG. 7 represents an example of an eye-tracking chart derived from the infra-red receiver signal.

FIG. 7 shows an example of the intensity (702) of the signal perceived by the IR receiver vs time (701). Each peak reflects a more or less complete closing of the eyelid. This exemplary diagram makes it possible to distinguish the palpebral movements corresponding to voluntary eye blinks, corresponding to higher intensity peaks, and more numerous peaks, of lower intensity, corresponding to spontaneous eye blinks.

Spontaneous eye blinks are fast movements of the eyelid, that a person is not aware of and whose physiological role is to avoid the desiccation of the surface of the eye by ensuring the collection and the excretion of the tears and the spread out of the lachrymal film.

These movements occur according to a variable frequency depending on the individual, of about 20 blinks per minute. The frequency and the speed of these blinks are influenced by factors such as the emotional stress, tiredness or the consumption of psychotropic substances, and accordingly constitute indicators adapted to the measurement of alertness.

Therefore, for the alertness analysis, only the peaks whose intensity is lower than a threshold (730) is considered. This threshold is set for a given individual, during an adjustment and calibration step of the eyeglasses.

According to a specific embodiment, voluntary eye blinks or winks, can be used to control functions, including functionalities of the object connected to the eyeglasses. When implementing such a possibility, only the peaks whose intensity is higher than an intensity threshold (730) and of a duration longer than a given time lapse are considered.

Figure 8:
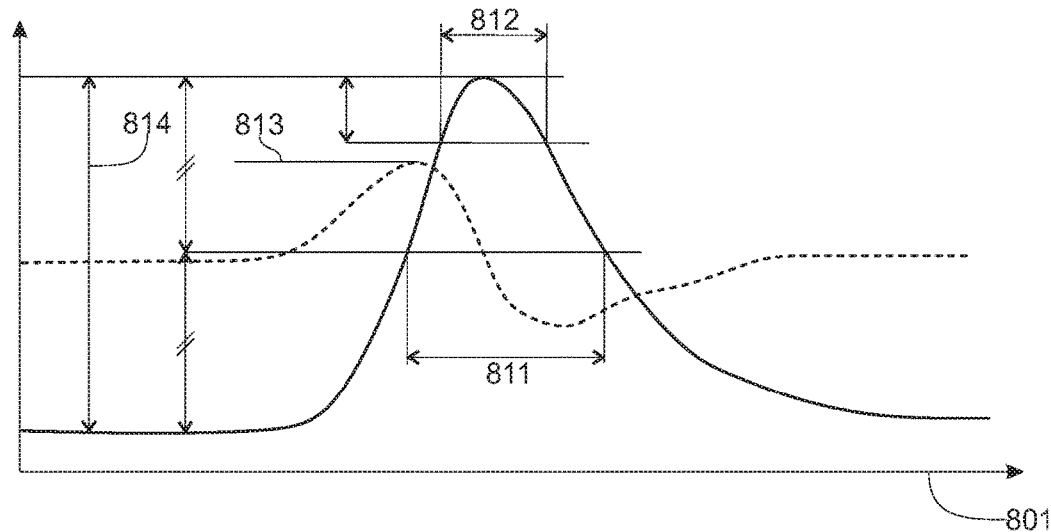
FIG. 8 shows the time evolution of the magnitude of the signal issued by the IR receiver as well as its derivative during a spontaneous eye blink.

FIG. 8, at the scale of a spontaneous eye blink, the analysis of the signal (802) issued by the IR receiver and of its time derivative (803), allows to define several parameters, such as:

the blinking duration (811) measured by the peak full width at half maximum or more specifically at the half of its maximum measured intensity;

the duration of closure at more than 80% of the eyelid (812); and the maximum closing speed (813).

Analyzing several peaks over a given time further gives access to:

the spontaneous blinking frequency, or more precisely the number of spontaneous blinking on a given time; and the relative amount of time spent with the eyelid closed at more than 80%.

The beginning of a peak is easily detected on the time derivative of the signal.

The derivation operation is however affected by the noise in the signal.

To this end, the signal from the IR receiver, is first filtered in order to eliminate the influence of ambient light, whether natural or artificial.

The part of the spectrum of the ambient light falling in the measurement range of the IR receiver affects the response of the sensor by adding noise and additional variation frequencies.

According to an exemplary embodiment, the influence of ambient light is thus eliminated from the signal by applying to this one a moving average polynomial filter, e.g., of the Savitsky-Golay type, followed by a filtering of the signal thus smoothed by a Butterworth's band pass filter, with a 10 Hz bandwidth, centered on the average frequency of spontaneous eye blinking.

The different stages of drowsiness are characterized by an increase in the relative time when the eyelids are closed over a given interpolation time, because of the increase in the eye blink frequency or the increased duration of each eye blink.

This feature is captured by the ratio of the total time spent with the eyelid closed at more than 80% (812) over an interpolation duration, further referred as PERCLOS$_{80}$.

According to an exemplary embodiment, this parameter is calculated over on interpolation duration of 20 seconds. For an alert individual this parameter is less than 3%. The increase of this ratio indicates the onset of drowsiness and the decrease of alertness. This 3% level is independent of the individual and so enables to reliably characterize a fully alert state of said individual, and to calculate for this state other parameters that better characterize the drowsiness state but are individual dependent.

The analysis of the decrease of alertness performed over a sample of people translates in an increase of the spontaneous eye blink frequency and in an increase of the dispersion of the interval of time between 2 eye blinks, in particular, because the duration of certain eye blinks lengthens.

The eye blinking frequency, and the time between two eye blinks, can be extracted from the IR receiver signal over a given interpolation time. However, if this parameter is statistically relevant over a sample of individuals, it is difficult to draw an actual early indicator of reduced alertness for a given individual because the behavior changes from one individual to another. Therefore, such an indicator can be reliably used only for detecting an advanced state of drowsiness, close to a slumber.

For this purpose, an indicator is calculated by considering the proportion of eye blinks having a duration of eye lid closure greater than a given value.

As a for instance, this threshold level is set at 0.3 seconds, and if for 10 successive peaks of eye blinks more than 6 have a duration (811), measured by the width of the eye blink peak, longer than this threshold, then the indicator takes the scalar value of 0.6 (6/10).

This 0.3 second duration and this proportion of 0.6 are high values, corresponding to a state of drowsiness just before falling in a slumber whoever the individual. Therefore, in the same way that the $PERCLOS_{80}$ parameter makes it possible to define, when it is lower than 3%, in a reliable way a fully alert state, the latter parameter, named $DURATION_{50}$, allows when it reaches a level of 0.6 to detect in a reliable way, a state of loss of alertness. The detection of these two extreme values, enables to define other thresholds, by a learning mechanism, related to other parameters that are more sensitive to alertness but more individual dependent.

The AVR parameter is defined by the ratio of the eye blink peak amplitude (814) to the maximum eyelid closing speed (813). This parameter is assessed for each peak of spontaneous eye blink over a given measurement time, e.g., 3 minutes.

Figure 9:
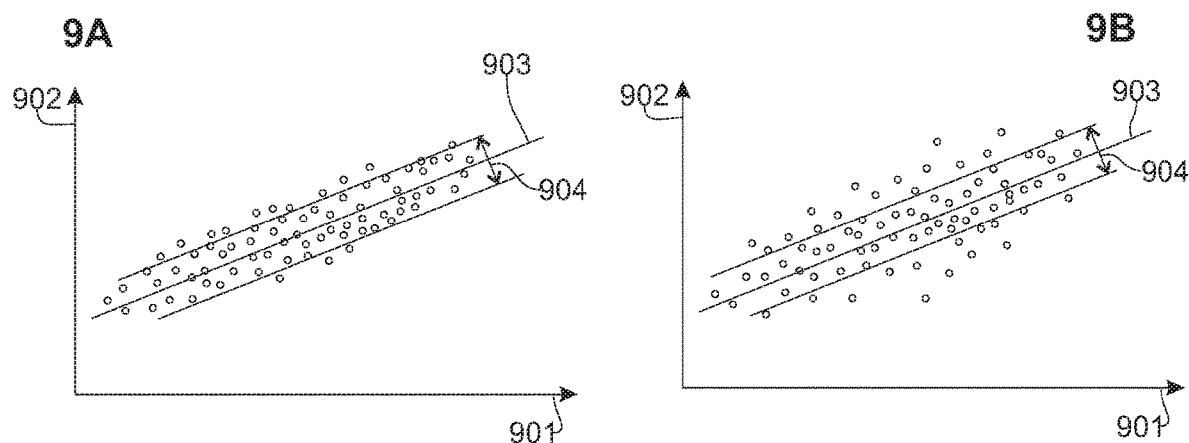
FIG. 9 represents the evolution of the AVR parameter with time, FIG. 9A for an awakened person, and FIG. 9A in the case of a drowsy person.

FIG. 9A, by plotting the successive values (902) of this parameter with time (901) for an alert individual, they line up substantially on a straight line (903). Starting from the dots cloud thus plot, a dispersion interval (904) is estimated for the alert individual, 90% of the cloud being comprised in this interval. The slope of the line and the width of the interval are individual dependent and for a same individual are likely to vary in time.

FIG. 9B, when the same individual, shows signs of reduced alertness, the variance of the AVR parameter measured over the interpolation time increases, which translates into measurement dots lying outside the interval calculated in the alert state for the same individual.

Thus, for instance, a scalar index of drowsiness/alertness is obtained by counting the number of times the assessed AVR value is out of the interval, over a given time, said interval boundaries being calculated when the individual is in an awakened state.

The interval must be calculated for each individual. For example, the line (903) equation and the interval (904) are calculated from the most recent AVR values that were assessed when the individual was in a confirmed awakened state, i.e., with a $PERCLOS_{80} < 3\%$, the corresponding data are stored and updated in the memory means of the processing and calculation unit.

Additional parameters derived from the accelerometer signal allows to detect and to characterize a head drop, its associated frequency or duration, these parameters being characteristic of an advanced drop of alertness.

According to an exemplary implementation, only the acceleration according to the direction of gravity is used, that is to say according to they axis in the embodiment shown FIG. 2.

In normal circumstances, the accelerometer measures an acceleration of 1 g directed according to the positive direction of the y axis and corresponding to the gravity.

Figure 10:
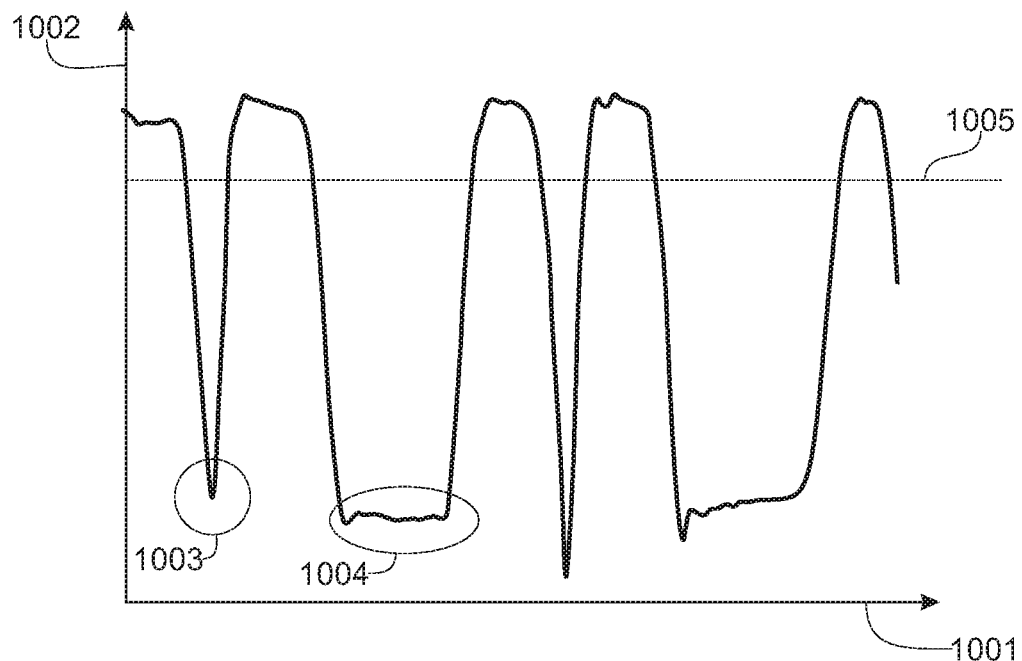
FIG. 10 shows an example of the evolution of the acceleration measured according to the direction of gravity during a head drop.

FIG. 10, on a diagram showing the variation of the acceleration on they axis (1002) vs time (1002), at the time of a significant drop of alertness (1003, 1004) translating in a micro slumber, the head of the individual falls forwards according to the neck joint of least resistance.

In the extension position, with the head leaning forward, the orientation of they axis compared to gravity makes that the projection of gravity acceleration on this axis is lower than 1 g, and then reaches 1 g again if the individual straightens its head. Therefore, a head drop (1003, 1004) is detected if the acceleration according to the y axis takes a value that is less than a threshold value (1005).

The signal is initially filtered by a low pass filter, with a cut-off frequency of about 2 Hz in order to remove from the signal the shakes related to the activity of the individual. Only a head drop lasting over significant duration is taken into account, e.g. lasting more than 0.2 second. Thus, a scalar parameter is for example determined by the number of head drop found over a given measurement time. A second scalar parameter corresponds to the number of head drop lasting more than a second and longer duration threshold (1004), for example longer than 0.5 or 1 second, counted over the same measurement time interval or a longer time interval.

These scalar parameters:

$PERCLOS_{80}$, $v_1(t)$;

$DURATION_{50}$, $v_2(t)$;

number of AVR points outside the forecast range, $v_3(t)$; and number of head drops and long-lasting head drops, $v_4(t)$, $v_5(t)$.

where t is the time, are calculated in real time and are combined into a composite index that reflects the state of alertness of the individual and from which the decision to generate an alarm is made.

The calculation principle of the composite index is similar whatever the type of risky situation whose detection is aimed, but uses different parameters depending on the type of detection sought.

A shown in the aforementioned example related to alertness assessment, the parameters considered for the composite index computation, combines at least one parameter that is individual dependent such as $v_3(t)$ and at least one parameter that is not dependent individual dependent, such as $v_1(t)$, $v_2(t)$, $v_4(t)$, $v_5(t)$ either taken alone or in combination.

According to an exemplary embodiment and depending on the nature of the detection sought, these parameters are whether scalar or binaries, in the latter case taking the value 0 or 1 (or −1, +1) depending on whether a specific pattern is detected or not in the signal.

Accordingly, the parameters issued from the signals processing, whether scalar or binaries, are functions of time and noted $v_1(t) \ldots v_n(t)$.

They are grouped in a M(t) vector:

$$M(t) = \begin{bmatrix} v_1(t) \\ \vdots \\ v_n(t) \end{bmatrix}$$

A severity composite index V(t) related to a risky situation is, e.g., defined as:

$$V(t) = A \cdot V(t-1) + B \cdot M(t),$$

where A and B are matrices of coefficients which are specific to the individual and that are weighting the influence of each parameter relative to one another.

According to a simple example of implementation, at the beginning ($t_0$):

$$V(t_0) = V_0 + B \cdot M(t_0),$$

$$B = \begin{bmatrix} \beta_{11} & \cdots & \beta_{1n} \\ \vdots & \ddots & \vdots \\ \beta_{n1} & \cdots & \beta_{nn} \end{bmatrix},$$

$A = [\alpha_1 \ldots \alpha_n]$, and $V(t)$ is a scalar.

The $\alpha_i$ and $\beta_{ij}$ factors as well as the equation used for the combination of the parameters for the calculation of the composite index, evolve with the machine learning process, notably by the data statistical analysis performed at the server level (411, FIG. 4).

Based on the level of the composite index, several alarm levels are triggered. Coming back to FIG. 2, a first level of alarm corresponding, e.g., to an early stage of alertness drop, leads to the light up of the led (282) either continuous or blinking. A second alarm level corresponding to a further loss of alertness, triggers the buzzer. A third level activates simultaneously the led and the buzzer, and if the system is configured to do so, sends a message to the connected devices in proximity with the connected object paired with the eyeglasses.

Figure 11:
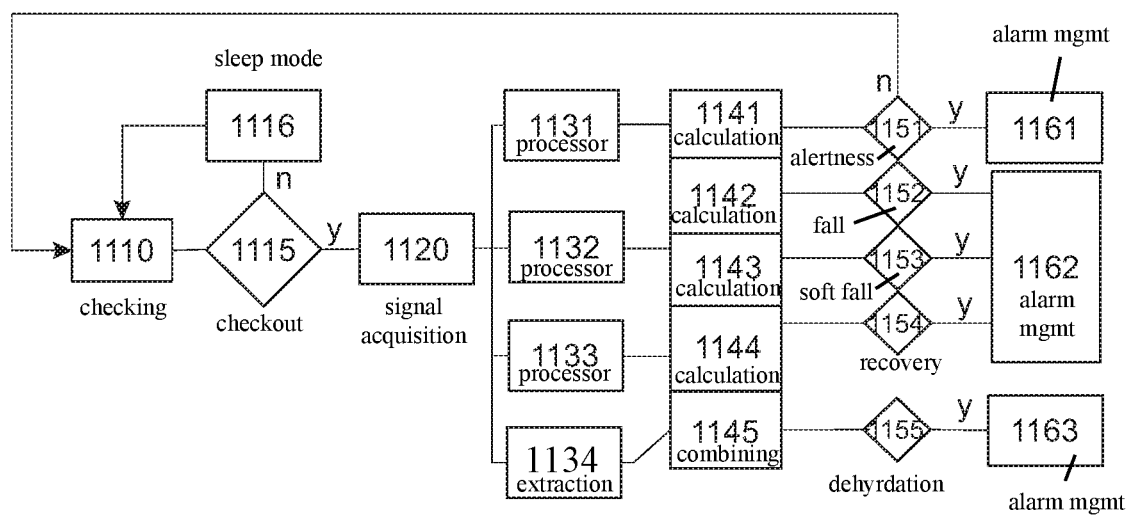
FIG. 11 is a flow chart of an exemplary signals processing and alarm triggering according to the method of the invention.

FIG. 11, according to an exemplary embodiment, the method of the invention comprises a first step (1110) for checking out the actual wearing of the eyeglasses. This step aims at ensuring the consistency of the further processing carried out, but also to turn the eyeglasses into a sleep mode if they are not used, in order to reduce the electrical consumption.

This check-out step, uses only the signal issued by the IR receiver using a specific filter and a specific processing. If the result of the check-out test (1115) is negative, the eyeglasses are turned (1116) in a sleep mode.

While in sleep mode, a check out test is performed on a regular basis, for example every minute, in order to activate the active mode, if the eyeglasses are detected as worn by the user. If the eyeglasses are detected as worn by the user, the signals acquisition (1120) is launched, this acquisition includes filtering operations specific to each signal. The acquisition is carried out at a sampling frequency ranging from 50 Hz to 150 Hz preferably around 70 Hz, who turns out to be a frequency to collect enough data to make the appropriate processing, while limiting the electrical consumption.

The signals thus conditioned are sent to processing modules (1131, 1132, 1133, 1134) which extract from said signals the specific and representative parameters either scalar or binaries. Thus, according to an exemplary embodiment, one of the modules (1131) is dedicated to the extraction of the parameters derived from the signal issued by the IR receiver. Another module (1132) is dedicated to the extraction of the parameters from the signals issued by the accelerometers, a third module (1133) is dedicated to the extraction of the parameters from the signal issued by the barometric sensor and a fourth module (1134) is dedicated to the extraction of parameters from the impedance measurement of the circuit comprising the electrodes.

The parameters resulting from this processing are combined in composite indexes, during a calculation step also implementing several modules, for example, a module for the calculation of alertness (1141) using the parameters derived from the processing of the signal issued by the IR receiver and at least one parameter resulting from the processing of the signal issue by the accelerometer, a module of calculation (1142) relating to the falls using the parameters resulting from the processing of the accelerometry signals and, according to a specific embodiment, those derived from the processing of the signal issued by the barometric sensor, a module of calculation (1143) relating to the falls known as soft, using parameters resulting from the processing of accelerometry and barometric sensor signals, a module of calculation (1144) relating to the recovery after a fall, using the parameters resulting from the processing of the accelerometry signals, the IR receiver signal and the signal from the barometric sensor, and a module (1145) combining the information derived from the IR sensor and the impedance measurement involving the electrodes for assessing dehydration.

Each module of calculation thus defines a composite index relating to the risky situation whose detection is aimed. Each of these composite indexes is compared to a threshold value that is stored in memory, that is to say an alertness test (1151), a fall test (1152), a soft fall test (1153), a recovery after fall test (1154) and a dehydration test (1155).

If the threshold value is passed an alarm request is addressed to an alarm management module (1161, 1162, 1163). According to this example, three alarm management modules are used. An alarm management module (1161) relating to alertness, that triggers an alertness alarm according to an alertness composite index as described above. An alarm management module (1162) relating to falls, which depending on the passing of a threshold pattern of the 3 composite indexes related to falls, triggers various means of alarm, considering all or part of the composite indexes of fall, soft fall, and recovery after fall, and an alarm management module (1163) related to dehydration.

If no threshold is passed, the acquisition and processing of the signals continue without change until a possible detection of an alarm condition. Therefore, starting from a common acquisition basis, carried out with a limited number of sensors and of processing modules (1131, 1132, 1133, 1134), the functionalities of the system are adapted to the needs by activating or loading the specific calculation and alarm management modules.

As for instance, if the user of system of the invention is young, healthy and not working in a dangerous environment, the main targeted features are alertness monitoring, for example when driving and dehydration. In such a case, the modules relating to the calculation and the alarm management relating to falls (1142, 1143, 1144, 1152, 1153, 1154, 1162) are not activated, although the information derived from the accelerometers remains used, in particular for the detection of a head drop. To the opposite, for an older person, not driving, the main risks to be covered are that of the fall and a dehydration. In such a case the alarm management modules relating to alertness (1141, 1151, 1161) are not activated, which however does not mean that information resulting from the IR receiver is not used, they are indeed used in the calculation module (1144) dealing with the recovery after fall, and also for dehydration measurement. Finally, for other specific cases, all the modules are activated.

Figure 12:
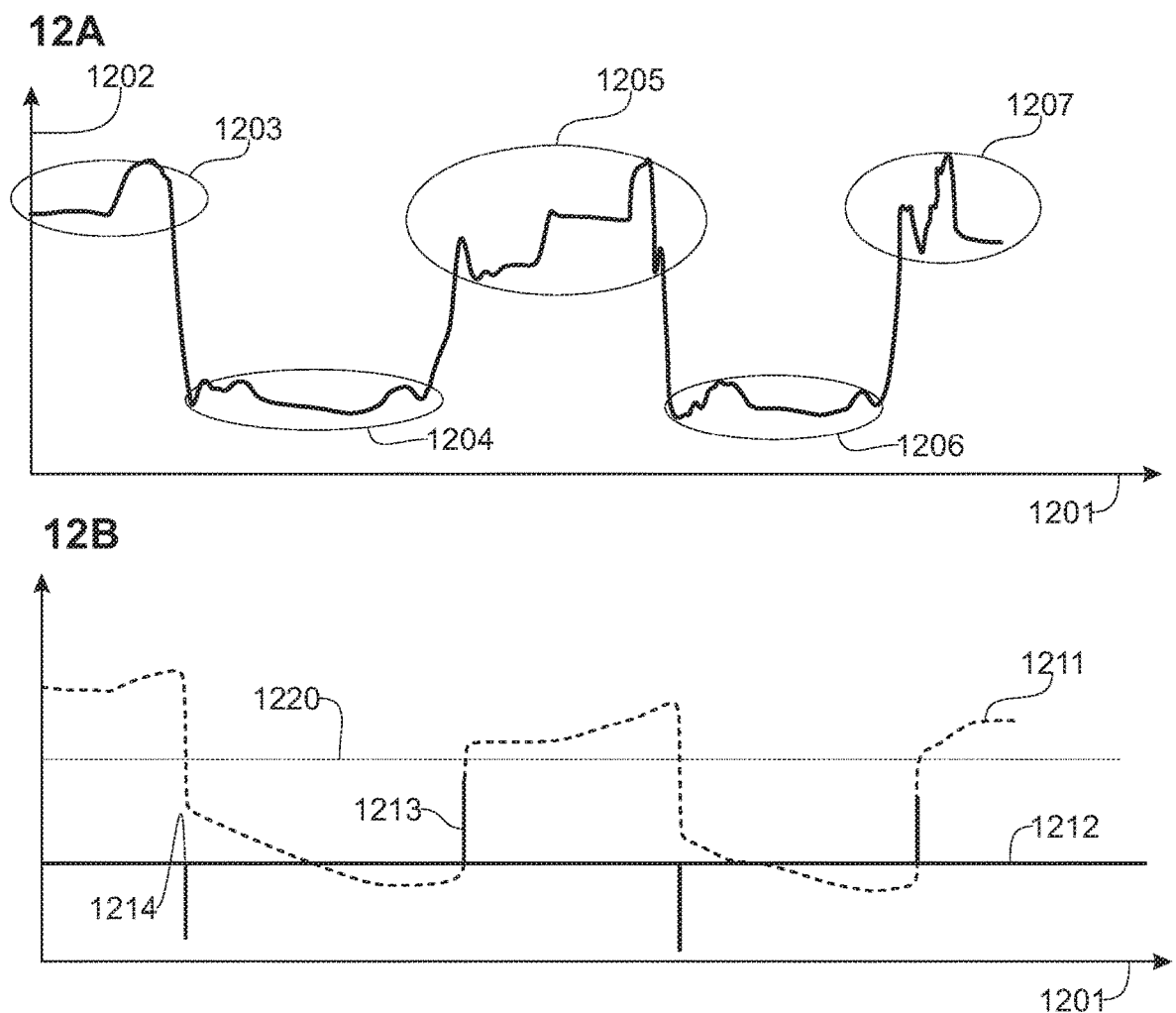
FIG. 12 shows the evolution of the signal issued by the IR receiver during wearing and take off of the eyeglasses of the system of the invention, in FIG. 12A the raw signal, and in FIG. 12B, the filtered signal and its time derivative.

FIG. 12, signals from the IR receiver are used to check out if the user actually wears the glasses.

FIG. 12A, when following the evolution of the intensity (1202) of the signal emitted by the IR receiver according to time (1201) during successive putting and withdrawal of the eyeglasses, when the glasses are removed (1204, 1206), the emitted infra-red beam is not reflected by the eyelid or the cornea and the signal intensity is low. On the other hand, as soon as the glasses are correctly worn (1203, 1205, 1207) by the user the reflection of the signal on the ocular area clearly increases the intensity of the signal.

FIG. 12B, according to an exemplary embodiment, in order to detect if the user is wearing or not the eyeglasses, the signal issued from the IR receiver is strongly smoothed (1211) for example by means of an exponential weighting moving average filter.

Using the time derivative (1212) of the filtered signal makes it possible to easily detect an event of taking off (1214) or putting on (1213) of the eyeglasses.

Alternatively, or in a complementary way, a threshold (1220) is defined so that the glasses are correctly worn by the user when the intensity of the signal (1211) thus strongly filtered, takes values higher than this threshold (1220). When the user does not wear the eyeglasses, for instance because they fell down following a fall, or when it does not wear them correctly, for example too ahead on the nose or when they do not rest on the two ears, the calculation of parameters, not only those issued from the IR receiver signal but also derived from the signals issued by the other sensors is erroneous.

Figure 13:
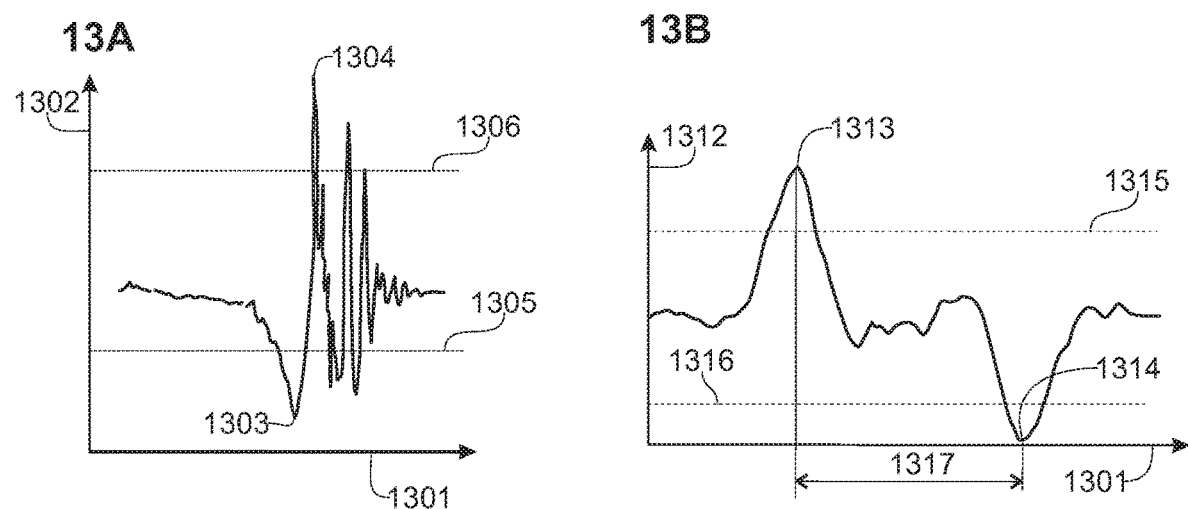
FIG. 13 shows examples of evolution of signals during a fall event, FIG. 13A the signal issued by the accelerometer, FIG. 13B the signal issued by the barometric sensor.

Therefore, the actuation of the sleep mode following the detection of the user not wearing or not properly wearing the eyeglasses is progressive and starts with the emission of a specific alarm, e.g., on the led and the buzzer and possibly on the connected object paired with the glasses. Then, during the periodic tests performed in the sleep mode, a short alarm is triggered if the glasses are still detected as not worn or incorrectly worn by the user, for example by a brief and simultaneous triggering of the led and the buzzer, for each test performed, e.g., within 15 minutes after the actuation of the sleep mode. Beyond this period, the system shifts to a deeper sleep mode where no alarm is triggered FIG. 13, for the detection of simple falls, the calculation of relevant parameters uses the accelerometer signals. The signals are initially filtered through a low pass filter with a low cut-off frequency, e.g., 0.1 Hz, in order to eliminate vibrations and phenomena corresponding to everyday life activities. According to an exemplary embodiment, a second filtering such as a moving median filter, preferentially of $3^{rd}$ order, is performed, this type of filter makes it possible to eliminate the random noise while preserving the peaks acuity. FIG. 13A, taking into account the positioning of the accelerometer, the gravity being directed according to the positive y axis, a first major effect of a fall is detected by a drop of the acceleration measured according to the y axis which is also detected on the sum of accelerations according to the three axes.

Thus, by plotting the evolution of the sum of accelerations (1302) according to the 3 axes of the accelerometer vs time (1301), a fall event is characterized by the appearance of a first peak (1303) directed in the negative direction and corresponding to the free fall phenomenon. That first peak is almost immediately followed by a second peak (1304) directed in the positive direction of the axis (1302) and corresponding to the impact of the body on the ground or on any other obstacle.

Therefore, the appearance of two consecutive inverted peaks in the sum of accelerations, in a given time window, each exceeding a threshold (1305, 1306), is a specific pattern indicative of a fall. As a for instance, the lower threshold value is set at 0.6 g (5.89 m·s$^{-2}$) and the upper threshold (1306), corresponding to the impact, is set at 2 g (19.62 m·s$^{-2}$).

These values are not user dependent and lead to a parameter of the binary type, translating whether or not such a pattern is detected over a given measurement time. With these threshold values, everyday life activities such as walking or stepping down a stairway do not generate a detectable pattern and thus do not generate any false alarm.

FIG. 13B shows evolution (1312) of the time derivative of the signal issued by the barometric sensor vs time during a fall event followed by a recovery where the person raises up again. A first peak (1313) corresponds to the fall, i.e., an altitude drop resulting in an increase in the measured atmospheric pressure.

The individual then remains on the ground for a certain time, thus the pressure stabilizes, then it raises up, which corresponds to a second peak (1314) of reduction of the pressure or increase in altitude.

These events occur over a longer time than the succession of acceleration peaks observed during a fall event. Therefore, a fall event is also characterized by a binary parameter, corresponding to the appearance of a positive peak (1313) in the time derivative of the barometric pressure whose amplitude exceeds a certain threshold A three feet (1 meter) free fall implies a pressure variation of 12 Pa over a duration of approximately 0.3 seconds. Actually, a fall is rarely completely free so that the threshold is for example set between 10 Pa·s$^{-1}$ and 20 Pa·s$^{-1}$. The corresponding characterization parameter is a binary parameter whose value depends on whether or not such a positive peak is observed over a given measurement time. The recovery after the fall can be detected by the appearance of a second peak (1314) inverted when compared to the first and which amplitude exceeds a threshold value, for example comprised between 5 Pa·s$^{-1}$ and 10 Pa·s$^{-1}$.

So, an additional parameter for the characterization of a fall is a binary parameter, indicating the presence of a recovery peak on the time derivative of the pressure signal in a given interval of time following the fall peak. Finally, an additional parameter, of scalar type, corresponding to the time (1317) separating the fall peak (1313) from the recovery peak (1314) on the time derivative of the pressure signal is also used to characterize the seriousness of a fall.

These parameters are combined into a composite index according to a similar principle to the one exposed for the measurement and detection of the loss of alertness, which composite index is used to trigger different levels of alarm.

The method exposed above is effective for detecting a fall involving free fall phenomenon, even of a short duration found in the case of an accidental fall or in the case of a sudden loss of consciousness.

However, in certain circumstances or for some people at risk, the fall can be caused, for example, by a progressive loss of consciousness, leading to a fall, known as a soft fall, not allowing to detect a free fall phenomenon. However, this type of fall is critical for some people at risk. If a free fall event can be detected by the peak (1303) directed according to the negative y axis, such a peak is not generally seen in the case of a soft fall, the peak of impact (1304) is however detected, although with a lower amplitude than in the case of an accidental fall.

The same applies for the signal corresponding to the time derivative of the barometric pressure, a peak (1313) corresponding to the altitude drop is well observed but less salient in case of a soft fall. Therefore, a soft fall is characterized by the appearance of an impact peak, detected on the sum of accelerations, with a lower threshold as compared to the case of a free fall, and by a positive peak in the time derivative of the pressure signal, also detected considering a lower threshold value. These two parameters are binary parameters reflecting the appearance of such peaks in the measurement interval.

However, using only these two parameters with lowered thresholds leads to a risk of detecting a negative false, i.e., to interpret as a fall a situation of the everyday life, like sitting down on a chair or in an armchair.

Figure 14:
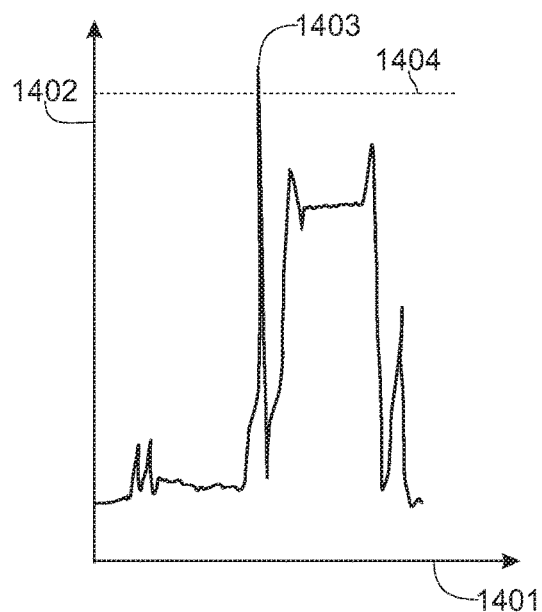
FIG. 14 shows an example of the evolution of the acceleration in a plane perpendicular to gravity during a soft fall event.

FIG. 14, to the difference of an everyday life situation like sitting down in an armchair, a fall, even a soft fall, implies a loss of verticality. The position of the glasses, on the head of the individual, is particularly advantageous to measure such a loss of verticality. The loss of verticality is measured for example by the value of the resulting acceleration in a plane perpendicular to the gravity, that is to say on the x and z axes while referring to FIG. 2. Thus, the plot of the intensity of acceleration (1402) in a plane perpendicular to the gravity vs time (1401) during a soft fall event, clearly reveals one or more peaks (1403) higher than a threshold (1404) which are thus detectable and whose detection over the acquisition time is captured in a binary parameter. These various parameters are combined in a composite index in order to detect a soft fall and to generate an alarm.

However, the combination of these parameters still does not make it possible to detect and characterize a soft fall during which the head remains appreciably vertical, as it is the case for a fall whereas the subject is leaned against a wall, or of another complex situation, leading to a negative or a positive false.

In order to cure these deficiencies, the complete algorithm for the detection and the characterization of the falls takes into account parameters determined in the moments following the fall and which generally attests of the recovery, or not, of the victim. These parameters allow, among other things, to reduce the rate of negatives false, more specifically in case of soft fall, by avoiding the generation of alarms and the notifying of rescue services in situations that are not justified.

As for instance, in addition to the time separating the fall from a potential recovery as defined in FIG. 13, a serious soft fall translates, for example, by a loss of consciousness of the individual. Such a loss of consciousness can be captured, in particular, by:

the individual remains staying in a nonconventional posture;
the individual does not exhibit a significant activity; and
the eyelid activity of the individual corresponds to a serious loss of alertness.

The posture of the individual can be determined for example by the values of the acceleration on the different axes of the accelerometer. When the person is motionless or quasi motionless the accelerometer is only subjected to the action of the gravity, which projects according to the positive y axis of FIG. 2 when the head is straight. Therefore, by measuring the acceleration components according to the 3 axes of the accelerometer, the orientation of the head is given. This orientation is defined by an angle compared to the theoretical vertical position of the head. The value of this angle is a scalar parameter, symptomatic of the posture of the individual after a fall.

The activity of the individual after a fall is also measured considering the signal issued by the accelerometer. If the individual moves, acceleration variations are observed. Therefore, the variation magnitude of the accelerations over a given time frame, measured for example by the variance of the acceleration signal over this time frame, is a symptomatic scalar parameter of the activity of the individual.

The measurement of the eyelid activity and the parameters which are deduced from it has been presented above.

Of course, the calculation of the activity parameters following a fall is not limited to the case of a soft fall but is also relevant in the event of an accidental fall.

The various parameters are combined in a composite index, according to the method exposed previously, the level of which is used to decide of the triggering of alarms.

In a specific but not exceptional case, the eyeglasses fall down from the head of the individual upon the fall or stay in an incorrect position on its face during a time following the fall. In such a case, even if a fall signature can be detected, the parameters characterizing the fall by the behavior of the individual in the moments following the fall are not measurable or are measured in an erroneous way.

Thus, according to an exemplary implementation, following the detection of a fall, the generation of an alarm based on the parameters assessed after the fall event comprises a check out of the correct wearing of the eyeglasses by the individual. If a not wearing or an incorrect wearing is detected, an alarm is generated and repeated during a defined time, as long as the glasses are not put on correctly. If after this defined time, in spite of the emission of the alarms, the eyeglasses are still not correctly worn, then it is possible that the person is not able to put them on back, and an alarm is triggered.

The dehydration state of an individual is given by the water content of the body of the person as a percentage of its weight, or Total Body Water (TBW).

When the assessed TBW crosses a predetermined threshold that is a function of the individual, the system generates an alarm indicating that the person has reached critical conditions in terms of dehydration.

The IR transmitter and the IR receiver may be used to measure the IR light absorption of the blood conveyed by the blood vessels in the eye, either under the sclera or in the eyelid. The pattern of absorption of IR light by the blood can be correlated to the hydration state of the person.

To this end, the emission power of the IR receiver is increased at regular time intervals, as for instance, every 10 minutes, in order to measure the IR absorption pattern of the blood and assess the hydration state of the person.

The reflectance of the eye is also a function of the hydration of the eye, which in turn is an indicator of the hydration state of the person. This reflectance is also measured by means of the IR transmitter and the IR receiver.

These parameters: IR absorption pattern of the blood and reflectance change from one person to another, therefore these parameters are individual dependent and a calibration is required for these measurements.

The impedance variation of the skin with hydration when the electrodes are supplied with a low voltage and high frequency alternative current results from resistance and capacitance variations of the skin with the hydration level. The impedance measurement is in the range of a few hundreds of ohms, e.gs. 200 to 500 ohms.

The impedance of the skin value corresponding to a well hydrated subject is dependent upon the voltage and the frequency of the current, but is weakly dependent on the individual. Therefore, a threshold may be defined, that is independent of the user and stored in the memory means of the device.

In an alternative embodiment, impedance measurement may be performed at various frequencies. Capacitance variation are more sensitive in the lower frequency range, i.e., in the kHz range, while resistivity influences the results in the 10 kHz range.

These two frequencies measurement may be performed either sequentially by the same set of electrodes or by two different sets of electrodes.

A drop of about 10% from the nominal value of the impedance thus measured, indicates a dehydration state.

Such measurement may be performed on regular time intervals, e.g. every 30 minutes.

The device and the methods specified above allow to address most of the risky situations a person, more particularly an elderly, may face.

The same set of sensors or part thereof may also be used in order to detect a more general fall prone situation without connecting specifically this situation to a loss of alertness or to a dehydration state.

The inventors found that such a fall prone situation may be correlated, when referring to an individual, with the evolution of parameters characterizing:
 a walking pace;
 a sit to stand, or STS, condition; and
 a head posture.
 More particularly parameters like:
 a step duration variability;
 a head posture while walking;
 a daily number of STS;
 a duration of a STS; and
 a STS peak acceleration along a gravity axis.
may be taken alone or in combination in order to compute one or more composite indexes characterizing a fall prone situation.

From an overall point of view, those parameters may also be used as a measure of the muscle tone of an individual and may be combined in one or more composite indexes characterizing the muscle tone of an individual wearing the eyeglasses, without departing from the invention.

All of these parameters may be computed from the signal issued by the triaxial accelerometer alone. Adding the information issued by a gyro sensor simplifies the computation of relevant parameters, and adding the barometric sensor improves the accuracy of STS detection and characterization.

In an exemplary embodiment the method of the invention computes 7 parameters and combine them in a composite index.

Figure 16:
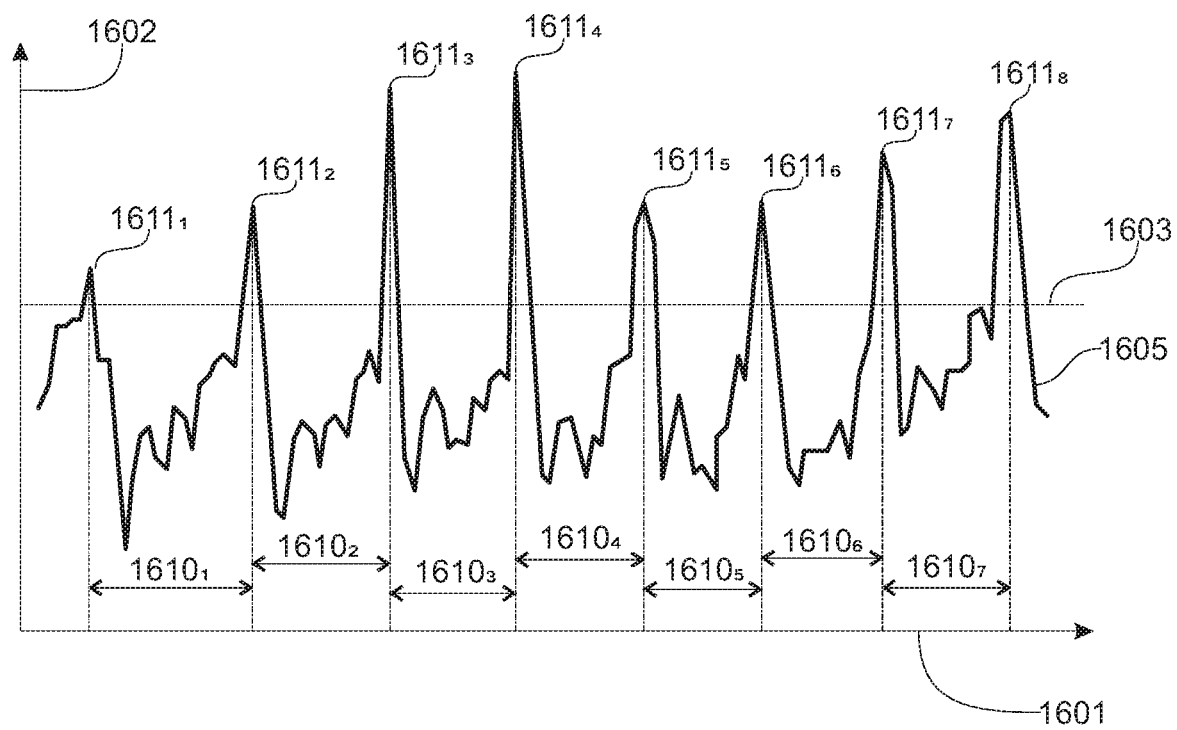
FIG. 16 shows an example of the evolution with time of an acceleration signal on an axis parallel to the gravity direction during a walking sequence.

FIG. 16, a first parameter for a fall prone situation detection is based on a variance of a walking step duration. To this end, the signal issued by the triaxial accelerometer is filtered by a low pass filter in order to limit the influence of events that are not related to the walk. As a nonlimiting example the a cut off frequency of the low pass filter is set to 4 Hz or under.

When looking at the amplitude of the acceleration (1602) along the gravity axis with time (1601) while the individual is walking, each time a foot hits the ground corresponds to a peak ($1611_1$ ... $1611_8$) exceeding a certain threshold (1603), e.g., 10 m/s². The time ($1610_1$ ... $1610_7$) separating two such consecutive peaks gives the duration of a step.

Looking to FIG. 2, the gravity direction is given by the y axis when the eyeglasses wearer is looking straight ahead. When the wearer head is leaning towards the front or towards the side, as shown hereafter, the direction of gravity will exhibit projected components on the x and z axes. Therefore, the component of the acceleration on the gravity direction, as considered in FIG. 16, is computed by the acceleration measured over the 3 axes of the triaxial accelerometer and using the head posture information, either derived from the signal of the accelerometer itself or using the information issued by a gyro sensor when the MEMS comprising the accelerometer includes such a sensor.

The triaxial accelerometer or the inertial MEMS are thus used as a pedometer. The computed filtered signal projected on the gravity axis is further designed as the "pedometer signal" (1605).

A first parameter is assessed by computing the step duration variance over a given number of consecutive steps.

To this end, once a peak ($1611_1$) crossing the acceleration threshold (1603) is detected on the pedometer signal (1605), said pedometer signal is scanned and recorded over a given duration or assessment time, called a walking sequence, and the number of consecutive peaks ($1611_2$ ... $1611_3$) is counted over this duration as well as the time ($1610_1$ ... $1610_7$) separating each peak.

The duration of the walking sequence in which the walking cadence is assessed may be set, as for instance, between 6 seconds and 15 seconds depending on the age and gender of the wearer, the older the longer.

The record is considered as valid provided that:
 the walking sequence comprises a minimum of consecutive peaks, e.g., 10 peaks, and
 the time separating any two consecutive peaks in the assessed walking sequence is lower than a predetermined value set depending on age and gender of the eyeglass wearer, typically between 900 ms and 1800 ms, the older the longer.

As an exemplary embodiment, provided that the sample walking sequence is valid, the variance of the time ($1610_1$ ... $1610_7$) separating 2 consecutive steps is computed over the sample and stored in the memory means of the eyeglasses along with the date (day and time) of the measurement. In a variant embodiment, the walking cadence, i.e., the number of steps over the walking sequence is also recorded, e.g. the number of steps per minute.

When the pair of eyeglasses is paired with a connected object as described above, the information may also be stored in the connected object memory means for archival purpose or to be anonymously transmitted to a server for further analysis either by the connected object or by remote means.

Such records may further be used to provide an indicator of the shape of an individual: a healthy individual walks at least a certain time a day, depending on its age, at a regular minimum pace, like 100 steps per minute, also depending on its age and gender. These indicators give an assessment of the shape of the individual, based on average population figures, while the analysis of the step duration variance and its evolution are more individual oriented.

Figure 17:
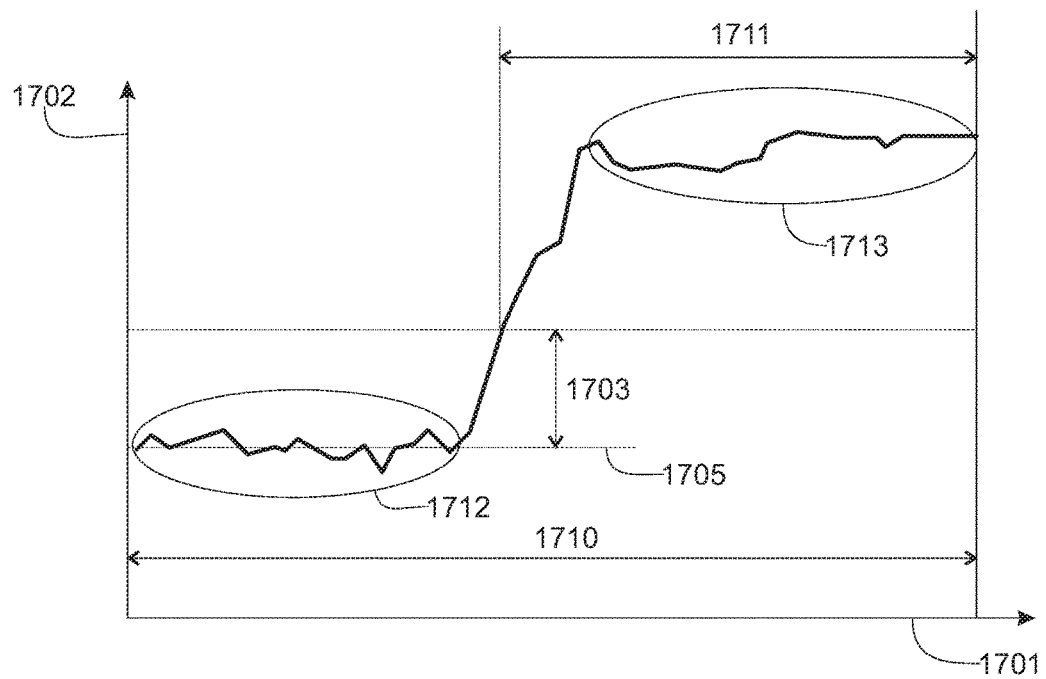
FIG. 17 shows a signal giving the evolution of a head posture during a walking sequence.

FIG. 17, in an exemplary embodiment, a second relevant parameter for a fall prone situation detection, is found to be the variation of the head posture during a walking sequence.

An individual will be more prone to a fall and will exhibit a lower muscular tone if its head is falling, chin to chest, during a walking sequence.

The position of the head of the individual during a walking sequence may be assessed using the information issued by the triaxial accelerometer itself, which according to the components of the acceleration over the 3 axes may be used to evaluate the orientation angle of the head (1702), more particularly its angle around the z axis of FIG. 2.

Alternatively or in combination, the head orientation of the individual may be assessed with the gyro sensor if the triaxial accelerometer is coupled with such a sensor in an inertial MEMS.

Looking at the variation of this head angle (1702) with time (1701) during a walking sequence allows to compute an additional parameter for a fall prone detection analysis. As a for instance, at the beginning (1712) of the walking sequence, the individual wearing the eyeglasses is looking straight ahead.

During the walking sequence the head posture progressively changes, the head falling front wise, the chin falling closer to the chest, to reach a final position (1713), where the head is clearly leaning.

As an exemplary embodiment a second parameter is defined as a ratio of the time (1711) during which the head of the wearer is leaning forward over a certain threshold angle (1703) by the duration (1710) of a valid walking sequence. The threshold (1703) is defined relative to an average posture (1705) of the wearer that may be set during a calibration process of the eyeglasses. The valid walking sequence duration (1710) is defined in the same way as detailed for the walking pace parameter assessment.

The parameter is recorded in the memory means of the eyeglasses along with the date. Additionally, when the eyeglasses are paired with a connected object, the information may also be recorded in the memory means of the connected object for archival or to be anonymously transmitted to a server for further analysis either by the connected object or by remote means.

In addition to this first set of parameters based on the analysis of a walking sequence, a second set of parameters is computed, based on the analysis of sit to stand movements of the individual wearing the eyeglasses.

Figure 18:
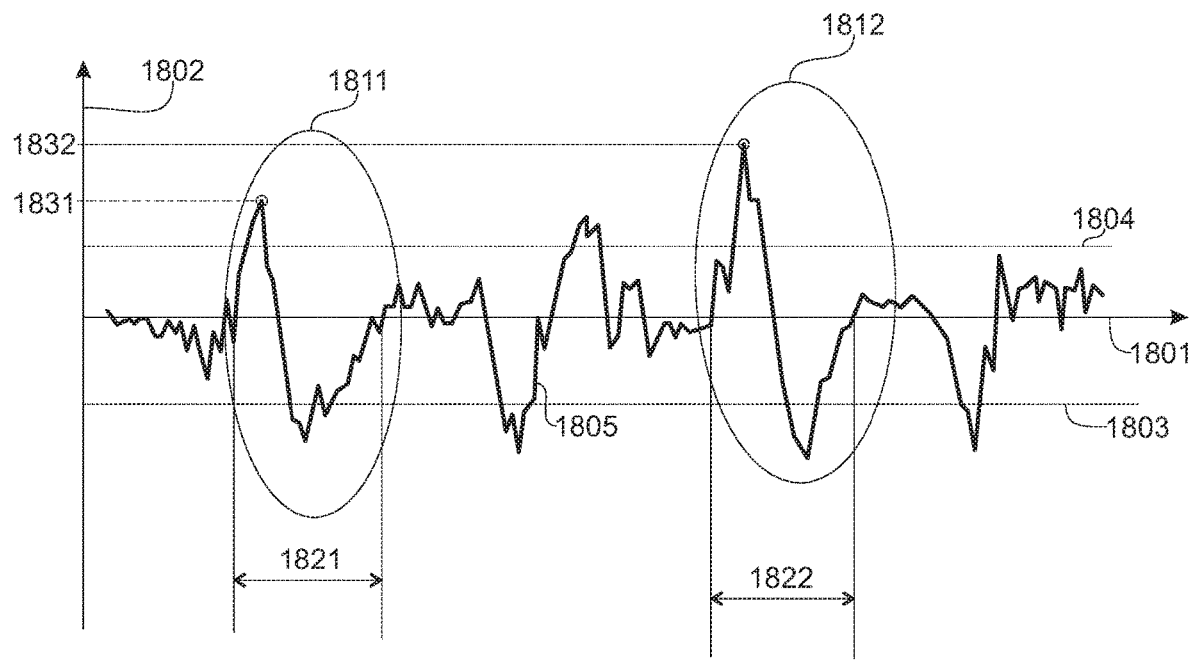
FIG. 18 shows an exemplary evolution with time of an acceleration signal parallel to the gravity axis featuring sit to stand events.

FIG. 18, a sit to stand movement may be detected by processing the triaxial accelerometer signals and considering the acceleration along the gravity axis.

A sit to stand, or STS event, is detected in the signal (1805) by a specific pattern (1811, 1812) when looking at the acceleration (1802) with time (1801), namely a peak up followed by a peak down.

In an exemplary embodiment, such pattern (1811, 1812) is taken into account if both peaks exceed or cross given thresholds (1803, 1804) which are set according to the individual and more specifically according to its age, said threshold crossings being observed in a maximum given time which is also set according to the age of the individual wearing the eyeglasses.

As a nonlimiting example, the thresholds (1803, 1804) on the acceleration peaks are set to +/−5 m/s$^2$ and the maximum time separating the crossing of these thresholds (1803, 1804) is set to 500 ms.

In addition, the signal issued by the barometric sensor may also be taken into account in order to detect a valid STS pattern.

Each detected STS is recorded with its date (day and time) in the memory means of the eyeglasses and additionally in the memory means of a connected object, if the eyeglasses are paired with such an object, along with parameters characterizing the STS event:
the duration (1821, 1822) of the STS event; and
the peak acceleration (1831, 1832) reached during the STS event.

From these records further parameters are computed, namely:
the daily number of STS events;
the day-to-day variation of the daily number of STS events;
the mean duration of STS events over a day; and
the standard deviation of the STS events duration.

A composite index is computed, as explained earlier, with the five above cited parameters and the 2 parameters derived from the walking sequences analysis, namely:
the variance of the steps duration; and
the head posture variation.

Such a composite index is compared to specific threshold values adapted to the age, the gender, the physical condition and the risk level of the individual.

According to an advantageous embodiment, the threshold values are also defined according to the time of the day, i.e., morning, afternoon, evening.

When the composite index crosses a threshold value, an alarm is generated. The alarm may be issued on the means of the eyeglasses but may also be sent to a caretaker or a relative of the individual wearing the eyeglasses.

Before being used effectively, the eyeglasses of the system must be adapted to their user.

This adaptation comprises a mechanical adaptation, in particular of the stems, and a calibration of the sensors, more particularly of the accelerometer and of the IR receiver.

The calibration is carried out by a professional, for example an optician, or by the user himself, guided by an application set up in the smartphone connected to the glasses.

The accelerometer calibration aims to determine accurately the gain on each of the axes and the rotation matrix so that the acceleration of the gravity is oriented according to the y axis when the user wears the glasses in a way considered to correspond to a vertical position of the head.

According to an exemplary embodiment, this calibration is performed using 3 acquisitions done in defined configurations. According to a first configuration, the eyeglasses are placed perfectly horizontal, in a position corresponding to the wearing position, for example in a bracket that is specially adapted for this purpose. In such a circumstance the y axis is supposed to measure a positive 1 g acceleration.

According to a second configuration, the eyeglasses are placed perfectly horizontal, in a position that is reversed from the wearing position, for example in a specific bracket. In such a circumstance they axis is supposed to measure a negative 1 g acceleration. In a specific embodiment the brackets used for these operations are part of the eyeglasses packaging.

In a third configuration the glasses are worn by their user in a right head position. The analysis of the three measurements carried out under these conditions makes it possible to caliber the accelerometer.

The calibration of the IR receiver consists in particular to set the threshold that allows to discriminate voluntary eye blinks from spontaneous eye blinks. According to an exemplary calibration method, the user wears the eyeglasses for a fixed period, e.g., 1 minute, during which it performs successive voluntary eye blinks at defined time intervals, e.g., every 10 seconds. During the acquisition phase, the system adjusts its setting, in order to detect 6 voluntary eye blink peaks and from 10 to 20 peaks of spontaneous eye blinks. The method may be repeated several times in order to check out the correct adjustment.

For calibrating the IR couples with regard to dehydration measurements, the subject must be well hydrated, which can be checked by using the impedance value. The emission power of the IR transmitter shall be set for both the measurement on the sclera and on the eyelid, as well as the level detected on the IR receiver.

These calibration operations are advantageously carried on a periodic basis.

Figure 15:
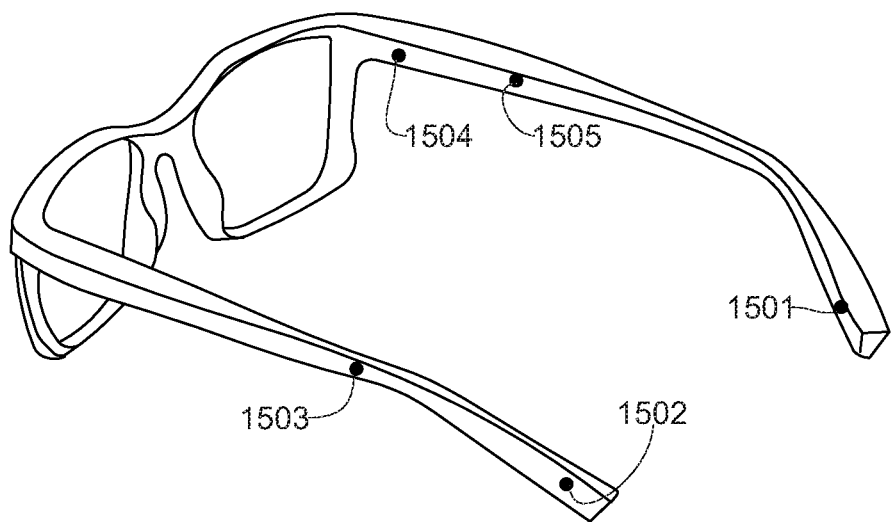
FIG. 15 shows, according to a perspective view, an exemplary embodiment of the arrangement of additional sensors in an enhanced version of the eyeglasses of the system of the invention.

FIG. 15, according to a specific embodiment, the eyeglasses of the system of the invention comprise additional sensors. This enhanced version allows to detect other risky situations. This paragraph and FIG. 15, only quote the sensors not previously described. As an exemplary embodiment the enhanced version comprises:

a thermometer (1501) to measure the body temperature; and
a heart pace sensor (1502).

These two sensors are advantageously placed on the stem ear pieces, behind the ears, for more reliable measurements:

a microphone (1503);
a blood pressure sensor (1504), coming in contact with the temple of the user;
the heart pace sensor (1502) is advantageously equipped with a photodiode to measure the blood oximetry; and
a blood glucose sensor (1505), for example, an infra-red sensor measuring the glucose level in the blood through the skin.

The description above and the exemplary embodiments show that the invention achieves its goal, namely to propose a customized system for monitoring the occurrence of a risky situation, using a discrete and aesthetic sensor.

The invention claimed is:

1. A method for preventing and detecting a fall of a user and implementing a system comprising:
a pair of eyeglasses with hinged stems including rims for supporting glasses, worn by the user and comprising a plurality of sensors and an alarm, the plurality of sensors being set in the hinged stems and the rims of the eyeglasses, wherein the plurality of sensors comprising:
a triaxial accelerometer;
an infrared (IR) transmitter and an IR receiver of infrared light both directed to a cornea of the user;
a barometric sensor;
wherein each of the triaxial accelerometer, the IR transmitter and IR receiver, and the barometric sensor of the plurality of sensors generates a different signal, and is connected to a microprocessor configured to execute a computer program stored in a memory to collect and analyze data issued by the plurality of sensors, and to trigger the alarm in response to an analysis of the data;
wherein the triaxial accelerometer generates a first signal that is acquired and processed to derive a walking pace parameter, a sit to stand parameter, a head posture parameter and an acceleration magnitude over three axes of the triaxial accelerometer;
the method comprising:
computing a first composite index based on the walking pace parameter, the sit to stand parameter and the head posture parameter; and
generating a first type of alarm in response to a determination that the first composite index exceeds a predetermined threshold;
acquiring a second signal of the barometric sensor;
computing a second composite index based on:
the acceleration magnitude combined along the three axes of the triaxial accelerometer;
a variance of the acceleration magnitude over a predetermined duration;
an acceleration component over an axis of the three axes of the triaxial accelerometer parallel to gravity;
the acceleration magnitude combined over the three axes of the triaxial accelerometer in a plane perpendicular to the gravity; and
a variation of a barometric pressure between two moments;
generating a second type of alarm corresponding to the detection of the fall of the user in response to a determination that the second composite index exceeds the predetermined threshold;
controlling the IR transmitter;
collecting and processing a third signal from the IR receiver to detect a closure and an opening of an eyelid of the user;
computing an alertness composite index based on the opening and closure of the eyelid of the user;
in response to the generation of the second type of alarm, computing a third composite index based on a body posture parameter derived from the head posture parameter and the barometric sensor, and the alertness composite index; and
generating a third type of alarm in response to a determination that the third composite index exceeds the predetermined threshold.

2. The method of claim 1, further comprising determining that the eyeglasses are worn by the user by performing a check out test that comprises activating the IR transmitter and analyzing the third signal of the IR receiver in response thereto.

3. The method of claim 1, wherein said computing the first composite index based on the walking pace parameter, the sit to stand parameter and the head posture parameter comprises:
projecting the first signal issued by the triaxial accelerometer on the axis of the three axes of the triaxial accelerometer parallel to a direction of the gravity to obtain a pedometer signal;
obtaining a threshold value and detecting consecutive peaks in the pedometer signal exceeding the predetermined threshold, during a predetermined assessment time;
measuring a separation time separating two consecutive peaks of the consecutive peaks during the predetermined assessment time;
computing a variance of the separation time over the predetermined assessment time; and
utilizing the variance of the separation time over the predetermined assessment time in computing the first composite index.

4. The method of claim 3, further comprising:
assessing an angle of a variation of the head posture parameter of the user during the predetermined assessment time;
obtaining a threshold angle and measuring a time the angle of the variation of the head posture parameter of the user during the predetermined assessment time exceeds the threshold angle; and
utilizing the time the angle of the variation of the head posture parameter of the user during the predetermined assessment time exceeds the threshold angle in computing the first composite index.

5. The method of claim 4, further comprising:
detecting a sit to stand event by a predetermined pattern in the first signal issued by the triaxial accelerometer on the axis of the three axes of the triaxial accelerometer comprising an acceleration parallel to the direction of the gravity;
measuring a duration of the sit to stand event;
measuring a peak acceleration during the sit to stand event; and
utilizing the duration of the sit to stand event and the peak acceleration during the sit to stand event in computing the first composite index.

6. The method of claim 5, further comprising:
counting a number of sit to stand events per day; and
utilizing the number of the sit to stand events per day in computing the first composite index.

* * * * *